(12) United States Patent
Allon et al.

(10) Patent No.: US 8,109,635 B2
(45) Date of Patent: Feb. 7, 2012

(54) INTEGRATED RETINAL IMAGER AND METHOD

(75) Inventors: Noam Allon, Haifa (IL); Israel Grossinger, Rehovot (IL); Michael Golub, Rehovot (IL); Moshe Bril, Beit Shemesh (IL)

(73) Assignee: Ophthalmic Imaging Systems, Sacramento, CA (US)

( * ) Notice: Subject to any disclaimer, the term of this patent is extended or adjusted under 35 U.S.C. 154(b) by 749 days.

(21) Appl. No.: 11/791,854

(22) PCT Filed: Aug. 11, 2005

(86) PCT No.: PCT/IL2005/000869
§ 371 (c)(1),
(2), (4) Date: Aug. 12, 2008

(87) PCT Pub. No.: WO2006/016366
PCT Pub. Date: Feb. 16, 2006

(65) Prior Publication Data
US 2009/0153797 A1 Jun. 18, 2009

Related U.S. Application Data

(60) Provisional application No. 60/600,810, filed on Aug. 12, 2004.

(51) Int. Cl.
*A61B 3/10* (2006.01)
(52) U.S. Cl. .......................................... 351/221
(58) Field of Classification Search .............. 351/221, 351/206, 246, 211, 205; 600/318, 319; 356/400; 250/461.1, 461.2
See application file for complete search history.

(56) References Cited

U.S. PATENT DOCUMENTS
4,660,945 A 4/1987 Trachtman
(Continued)

FOREIGN PATENT DOCUMENTS
WO 2004082465 A2 9/2004

OTHER PUBLICATIONS

Israeli Office Action mailed Mar. 28, 2010, from corresponding Israeli Patent Application No. 182611, two pages.
(Continued)

*Primary Examiner* — Hung Dang
(74) *Attorney, Agent, or Firm* — The Nath Law Group; Susanne M. Hopkins; William L. Klima

(57) ABSTRACT

A system and method are presented for use in imaging the patient's retina. A light source unit is provided including a light emitting diode (LED) arrangement comprising multiple LEDs of different wavelength ranges. A light guide arrangement is used with the LEDs arrangement and is configured for coupling light from the LEDs and providing output light beams of a desired shape. The illuminating light is directed towards a region on the retina, and light returned from the illuminated region is collected and directed to an image detector unit. The invention enables the use of LED light at high intensity as required in the eye retina imaging, while maintaining the required high-quality imaging. Also, the invention provides for simultaneous or quasi-simultaneous as well as high-speed imaging in FA and ICG imaging procedures, thereby satisfying a long felt need in ophthalmology. Also, the invention provides for automated illumination or light exposure control to optimize overall light exposure to the patient eye and best acquired image quality in terms of brightness, contrast and image signal-to-noise ratio.

53 Claims, 18 Drawing Sheets

U.S. PATENT DOCUMENTS

| | | |
|---|---|---|
| 5,374,193 A | 12/1994 | Trachtman |
| 5,742,374 A | 4/1998 | Nanjo et al. |
| 6,142,629 A | 11/2000 | Adel et al. |
| 6,685,317 B2 | 2/2004 | Su et al. |
| 6,690,466 B2 | 2/2004 | Miller et al. |
| 7,677,730 B2 * | 3/2010 | Shimizu .................. 351/206 |

OTHER PUBLICATIONS

European Patent Application No. 05764612.7, Office Action dated Sep. 19, 2011.

* cited by examiner

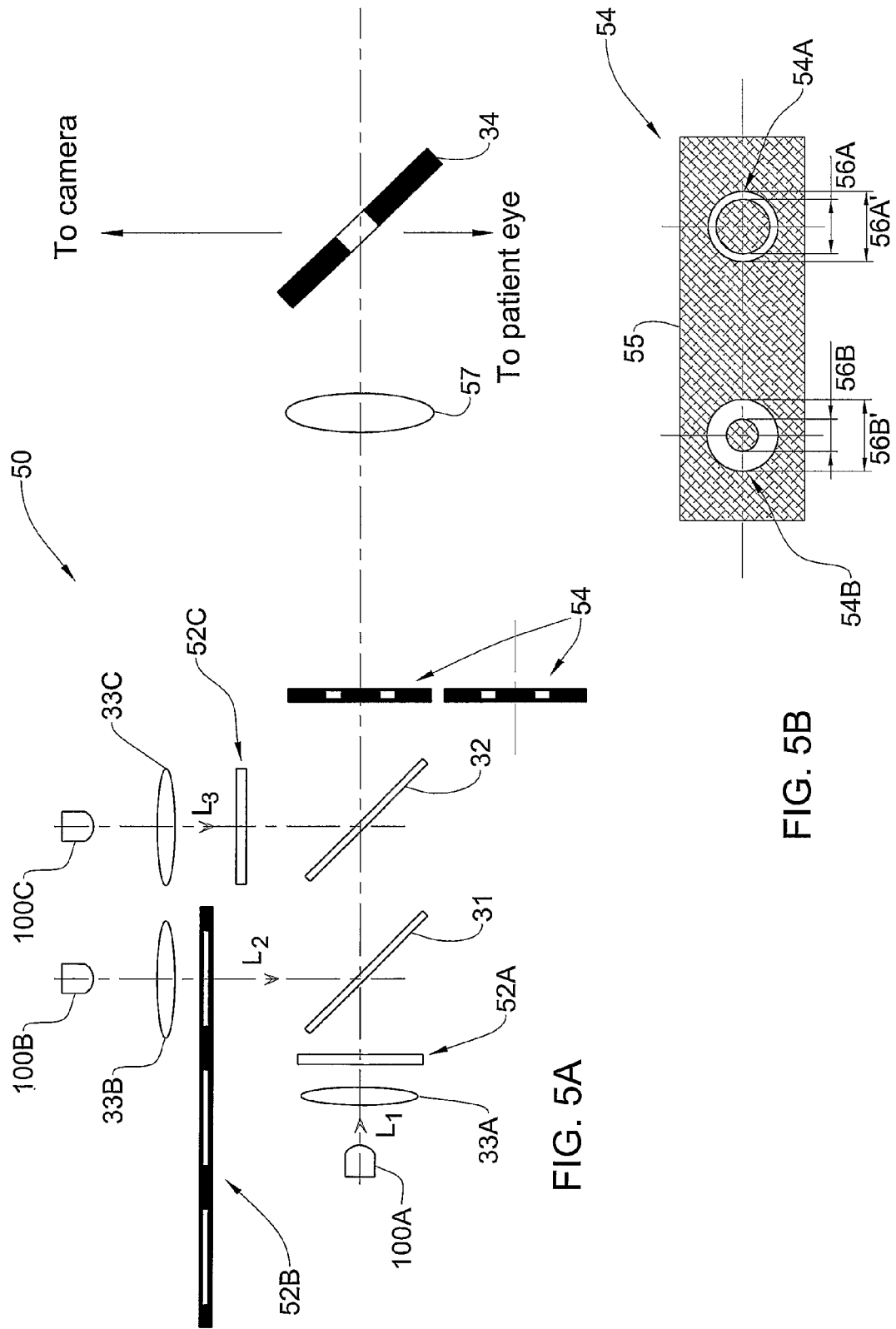

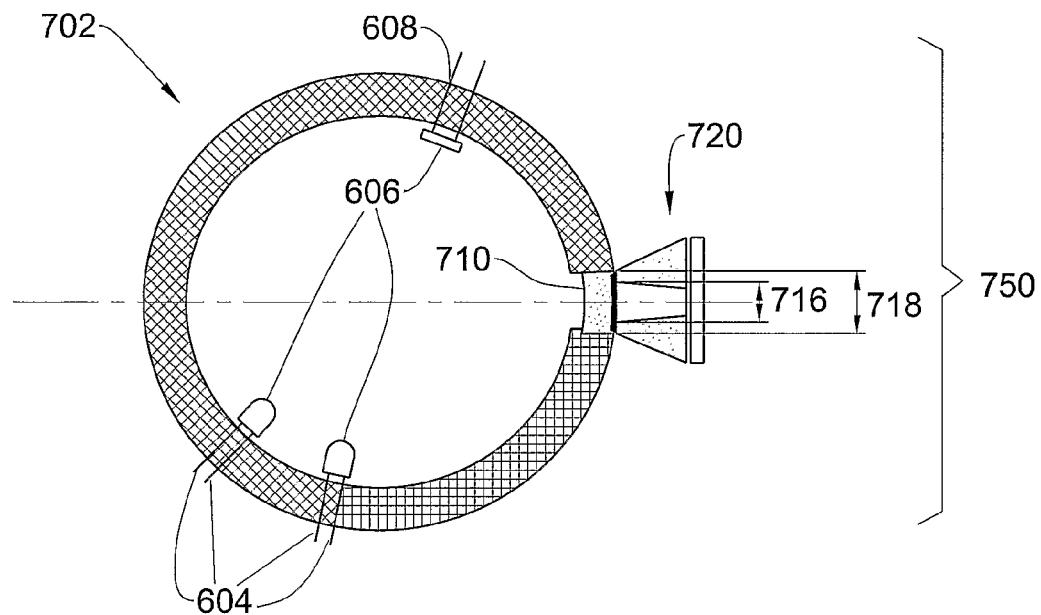
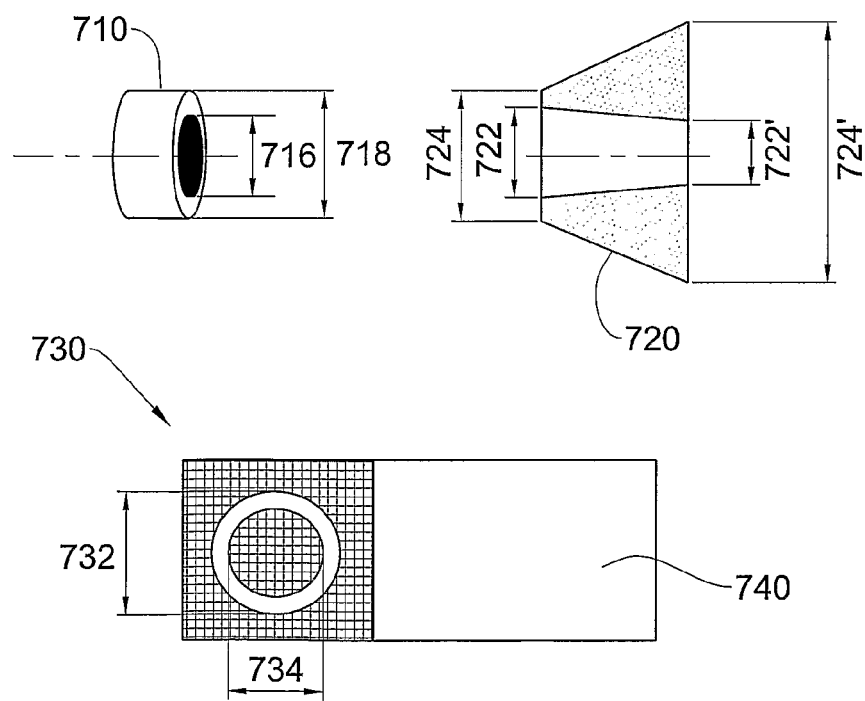
FIG. 11

INTEGRATED RETINAL IMAGER AND METHOD

Cross-Reference

This is a National Phase Application filed under 35 U.S.C. 371 of International Application No. PCT/IL2005/000869, filed Aug. 11, 2005, claiming the benefit under 35 USC 119(e) of U.S. Provisional Application No. 60/600,810, filed Aug. 12, 2004, the entire contents of each of which is hereby incorporated herein by reference in its entirety.

FIELD OF THE INVENTION

This invention is generally in the field of optical monitoring techniques, and relates to an imaging system and method, particularly useful in ophthalmology for retinal imaging.

BACKGROUND OF THE INVENTION

An imager used to take pictures of the retina is known as a fundus camera. These cameras could be used in fundus (retinal) photography and fluorescence angiography procedure. The latter is a retinal examination procedure where fluorescein dye is injected into a patient vein and a fundus camera is used to record images of the retina to reveal retinal blood circulation disorders, such as leakages, hemorrhages, edema and other pathologies.

Roughly speaking, there are two kinds of fundus cameras: mydriatic fundus cameras utilizing continuous illumination of the retina with visible light to permit focusing and non-mydriatic fundus cameras utilizing illumination of is the retina with invisible light, such as infrared light, which advantageously is not seen by the patient and therefore does not cause the contraction of the iris during the alignment procedure. Non-mydriatic cameras can be used in cases where dilation of the eye is not possible or in cases, such as screening of the retina, since in those cases following the positioning using invisible light a single high-intensity image of higher illumination (usually white) intensity is used per each patient eye. With the mydriatic fundus camera approach, it is necessary to apply a pupil-dilating (mydriatic) medication to the cornea in order to avoid contraction of the pupil in response to visible light to enable full visualization of the entire retina throughout the clinical procedure. In the non-mydriatic fundus camera, which allows focus on the retina in the naturally dilated state of the pupil, the eye is illuminated by infrared light and a continuous image is formed on an infrared imaging device or the light sensing plane of an infrared sensor such as a CCD or CMOS video camera.

The presently available high-performance fundus cameras typically use Halogen illumination or Xenon-Flash light to obtain various white light, single wavelength light (Red, Green, and Blue—using filters), fluorescein (FA) and Indo-Cyanine Green (ICG or ICGA) fluorescence images.

Clinically, there is a need to follow the fluorescence process throughout the life-cycle of the fluorescence agent, and especially during the initial phase of the agent entering the retinal and choroidal blood circulation. Due to the limitation of current technology in fundus cameras, only 1 or 2 Xenon-flash based images per second are possible to obtain, because of limitations of the energy sources to the Flash devices. Only laser beam based scanning devices (known also as SLO—Scanning Laser Opthalmoscopes) are able to record such events, with the limitation of smear and motion of the eye during image acquisition, causing limitation in image quality of the retina image.

Various techniques have been developed aimed at improving the performance of a fundus camera. For example, U.S. Pat. No. 5,742,374 discloses a fundus camera for photographing fundus of an eye to be examined. According to this technique, an observing illumination/target projection optical system utilizes a slit-plate having a pin-hole aperture and a ring-slit. The eye to be examined is illuminated with a ring-slit illumination to facilitate alignment and focusing.

The use of LED based illumination in a fundus camera has been proposed, and is described in U.S. Pat. No. 6,685,317. Here, a digital camera is described that combines the functions of the retinal camera and corneal camera into one, single, small, easy-to-use instrument. The single camera can acquire digital images of a retinal region of an eye, and digital images of a corneal region of the eye. The camera includes a first combination of optical elements for making said retinal digital images, and a second combination of optical elements for making said corneal digital images. In a preferred embodiment, a portion of these elements are shared elements including a first objective element of an objective lens combination, a digital image sensor and at least one eyepiece for viewing either the retina or the cornea. Also, preferably, the retinal combination also includes a first changeable element of said objective lens system for focusing, in combination with said first objective element, portions or all of said retinal region at or approximately at a common image plane. Also, preferably, the retinal combination also includes a retinal illuminating light source, an aperture within said frame and positioned within said first combination to form an effective retinal aperture located at or approximately at the lens of the eye defining an effective retinal aperture position, an infrared camera for determining eye position, and an aperture adjustment mechanism for adjusting the effective retinal aperture based on position signals from said infrared camera. Also, preferably, the cornea combination of elements includes a second changeable element of said objective lens system for focusing, in combination with said first objective element, portions or all of said cornea region at or approximately at a common image plane.

According to the technique of U.S. Pat. No. 6,685,317, light from a large area is collected by a fiber optic bundle. High power LEDs emit over a wide angle typically ±90 degrees. However, it appears that the optical setup described in this patent suffers inter alia from losing the majority of light due to the very small acceptance angle of commercially available fibers.

SUMMARY OF THE INVENTION

There is a need in the art to facilitate imaging of the retina by providing a novel imaging system and method, capable of providing an efficient coupling and directing of light to the region of interest (retina) of the eye, thereby enabling to reach high intensity illumination required to improve the image brightness and diagnostics by means of higher contrast level of the image. Also, an imaging system is to be fully controllable and yet compact in size.

The main idea of the present invention consists of enabling the use of LED light at high intensity as required in the eye retina imaging, while maintaining the required high-quality imaging. To this end, the present invention provides means for effectively coupling the maximal LED energy all along the illumination and imaging channels. Also, the present invention is aimed at providing simultaneous or quasi-simultaneous FA and ICGA imaging, thereby satisfying a long-felt need in ophthalmology.

The present invention provides a novel illumination/imaging system and method for use in an Integrated Retina Imager (fundus camera) that utilizes a LED-based light source. The technique of the present invention enables the LED-based illumination of a region of interest with desirably high intensity comparable with the known Xenon-flash based illumination. The present invention also provides for a novel LED flash capability technique.

According to one broad aspect of the invention, there is provided a system for use in imaging the patient's retina, the system comprising: (a) a light source unit comprising a light emitting diode (LED) arrangement comprising multiple LEDs of different wavelength ranges; (b) a light guide arrangement configured for coupling light from the LEDs and providing output light beams of a desired shape; (c) a light directing optics for directing the light beam towards a region on the retina and for collecting and directing light returned from the illuminated region to an image detector unit.

Preferably, the light source unit is configured for producing at least one ring-like shaped light beam.

The LED arrangement may include at least one LED emitting light in a near infrared spectral range, and/or at least one LED emitting light in a visible spectral range, for example for emitting light of Red, Green, Blue and White colors. The light source unit may also include at least one laser diode.

The system may include a wavelength-selective arrangement formed by one or more wavelength-selective filters (dichroic mirror or mirrors). The latter is appropriately accommodated for combining light from different LED assemblies.

The light directing optics includes an objective lens arrangement, and an imaging lens arrangement, and optionally also a condenser lens arrangement in the optical path of light emitted by the LED arrangement. In some embodiments of the invention, the light directing optics also includes a field lens arrangement in the optical path of the illuminating light, and/or a relay lens arrangement in the optical path of the illuminating light.

In some embodiments of the invention, the LED arrangement includes at least one LED unit formed by a LED and its associated light guide unit configured as a cone-like reflector. The light guide unit is preferably configured to produce the illuminating light beam cone with an angle of about 20-degrees or less.

In some embodiments of the invention, the light source unit is configured to couple light from each of the multiple LEDs into its dedicated fiber or fiber bundle. This may allow for enhancing the illuminating light.

In some embodiments of the invention, a ring-like member is used for carrying ends of the multiple fibers arranged along this ring-like member. The opposite ends of the fibers are coupled to the LEDs, respectively. By this, the ring-like light output from the ring-like member is defined. The central hole of the ring-like member may define an imaging channel. The system configuration may be such that at least one of the LEDs is coupled to its associated fiber via a lens arrangement. The fibers may be configured for guiding the light of different wavelengths from the different LEDs. The different wavelengths' fibers may be arranged within the ring-like member so as to reach substantially equal spectral distribution for as small as possible sub-section of the ring-like member. The LEDs may be arranged in a matrix, and may be coupled to their dedicated fibers, respectively, via a lenslet array, such that each lens element of the lenslet array is dedicated to couple one LED to one fiber or fiber bundle.

The LED arrangement may include at least two LED assemblies, each formed by the multiple LEDs coupled via the fibers, respectively, to the ring-like member. The multiple ring-like members may be arranged (e.g., mounted on a rotatable wheel) so as to enable selectively bring one of the ring-like members to the illuminating optical path.

The light directing optics may include a beam combiner in the form of a mirror with hole. Such a mirror reflects the illuminating light by its periphery reflective region, and transmits the returned light through the central hole. The hole diameter is defined by the eye pupil size and by the magnification of an objective lens arrangement.

The system of the invention provides for using an aperture, formed by the ring-like shaped light beam, as an imaging channel for the returned light to propagation.

In some embodiments of the invention, a mask assembly is used being located in the optical path of the illuminating light propagating to the beam combining mirror. The mask assembly is configured to define at least two masks of different patterns, each pattern defining a ring-like shaped light transmitting path.

In some embodiments, the light source unit includes diffractive or refractive optics accommodated in the optical path of light emitted by at least one LED. Such refractive or diffractive optics provides high efficient coupling of Lambertian light into a ring, thereby producing the ring-like shaped light beam.

The light source unit preferably includes an adaptor unit carrying the LED arrangement and configured and operable for selectively shifting one or more of the LEDs into an operation mode. The adaptor unit may be configured as follows: includes at least one first light unit formed by the first light guide unit carrying at its one end the first LED operating in a near infrared range and its other end carrying a first condenser lens arrangement; and at least two second light units each formed by the second light guide unit carrying at its one end the second LED operating in a visible spectral range and carrying a second condenser lens arrangement. The second light unit is arranged along an axis intersecting with the first light unit thereby enabling to combine the first and second light paths. The second light units are mounted on a member rotating with respect to the first light unit. Preferably, the adaptor unit includes a wavelength-selective arrangement accommodated at the intersection between the first and second optical paths. The adaptor unit preferably includes the multiple second light units containing the LEDs emitting different wavelengths of the visible range.

In some embodiments of the invention, the light source unit includes at least one LED assembly formed by multiple LEDs associated with a common light guide. The latter is configured for coupling light from the multiple LEDs into the single ring-like light beam.

The system may include one or more ring-like shaped members, each carrying the multiple LEDs of at least one LED assembly. This creates a ring-like shaped light source formed by the LEDs arranged in a circular array. The LEDs in the circular array may differ in emitting spectra and/or power; or may contain different groups of LEDs, the LEDs of each group being substantially identical in spectrum and/or power, different from that of the other group.

A condenser lens arrangement may be used with at least some of the LEDs to narrow an emitting angle of light. A light diffusing element may be used with at least some of the LEDs to provide substantially uniform illumination of the light beam. A micro lens array may be used to condense or diffuse light emitted by the LEDs in the circular array.

In some embodiments of the invention, the light source unit includes an integrating sphere (at least one such sphere) that carries the multiple LEDs. The sphere is formed with a ring-like window for the light output, and is configured to recycle light emitted by the LEDs by internal reflection in the integrating sphere. The inner surface of the window may be formed with a reflective coating. An external mask may be used being positioned so as to cover an inner diameter of the window. A light guide may be used being accommodated at the window and configured for narrowing light exit angles of the ring-shaped window to match those acceptable by an objective lens arrangement. The integrating sphere may contain light from multiple different wavelength channels; or alternatively (or additionally) a wavelength-selective arrangement may be used for combining light of different wavelengths from different LED assemblies.

The system may include LEDs emitting light of fluorescence exciting and visible wavelength ranges. In this case, a spectral filter is appropriately accommodated in the optical path of the returned light. The spectral filter may be configured for transmitting excited light, and blocking the exciting light. Such a spectral filter is displaceable between its operating position being in the optical path of returned light and its inoperative position being outside of said optical path. Alternatively, the spectral filter may be configured as a dual spectrum barrier filter defining two spectral bandwidths corresponding to those used for, respectively, fluorescein (FA) and Indo-Cyanine Green (ICG) angiography, thereby enabling to obtain a combined FA/ICG photo by applying visible illumination and NIR flashes simultaneously. In this case, the image detector unit includes a CMOS or CCD detector sensitive to a 400-850 nm spectral range.

In some embodiments of the invention, the light source unit includes one or more LEDs operating in a pulse (flash) mode. The pulse mode light source unit is operable with 30 or more frames (images) per second. Additionally, the light source unit may include one or more LEDs operating in a continuous illumination mode. In such embodiments, a control unit (connectable to the light source unit and to the image detector unit) is used being configured for analyzing images acquired with the pulse and continuous modes to set appropriate light exposure in either one of the application modes. The control unit is preferably configured to analyze data indicative of the images acquired with the continuous light mode to utilize this data for predicting amount of light exposure to be used in the pulsed mode imaging.

According to another broad aspect of the invention, there is provided a light source unit for use in an imaging system for imaging the patient's retina, the light source unit comprising one or more assemblies each including multiple, light emitting diodes (LEDs) arranged for producing a ring-like shaped light beam, each LED being coupled to one end of its dedicated optical fiber or fiber bundle, the other ends of the fibers or fiber bundles being attached to and arranged along a ring-like member, allowing to use a central hole of the ring-like member as an imaging channel for passing therethrough light returned form an illuminated region.

According to yet another broad aspect of the invention, there is provided a light source unit for use in an imaging system for imaging the patient's retina, the light source unit comprising at least two LED based assemblies emitting light of different wavelength ranges; a wavelength-selective assembly comprising at least one wavelength-selective filter accommodated in optical paths of illuminating light beams produced by said at least two LED based assemblies for combining said light beams into a single illuminating light path; a mask configured to define a variable pattern in said combined optical path to affect the light beam impinging thereon to produce therefrom a ring-like shaped light beam.

According to yet another broad aspect of the invention, there is provided a light source unit for use in an imaging system for imaging of a patient's retina, the light source unit comprising a support assembly configured for supporting at least one first LED based unit emitting light of a first wavelength range; at least two second LED based units for emitting light of at least two different second wavelength ranges; the LED based unit comprising one or more LED associated with a dedicated light guide configured to produce from light emitted by the LED a ring-like shaped light beam; the second light guide extending along an axis intersecting with an axis defined by the first light guide, the second light guides being mounted on a member rotatable with respect to the first light guide, thereby enabling to selectively locate a selected one of the second light guides in an operative position to combine optical paths of light emerging from the first light guide and light emerging from the selected second light guide.

According to yet another broad aspect of the invention, there is provided an imaging system for use in imaging the patient's retina, the system comprising: (a) a first camera operable with pulse mode illumination; (b) a second camera operable with continuous mode illumination; and (c) a control system connectable to the first and second cameras and configured for controlling the operation thereof by analyzing either pulse mode or continuous images or both of them and utilizing reference data indicative of the images corresponding to certain exposure parameters and determining optimal exposure parameters for either the pulse of continuous illumination or both of them.

According to yet another broad aspect of the present invention, there is provided a method for use in imaging the patient's retina, the method comprising producing light of multiple different wavelengths emitted by a light emitting diode (LED) arrangement; passing the emitted light through a light guide arrangement configured for coupling light from the LEDs and providing one or output light beams of a desired shape; directing said output light towards a region on the retina and collecting light returned from the illuminated region through the same objective lens arrangement; and imaging the collected returned light onto an image detector unit.

According to yet another broad aspect of the present invention, there is provided a method for controlling the operation of a fundus camera, the method comprising: providing predetermined exposure settings for pulse (flash) light illumination and continuous light illumination; providing data indicative of images acquired by a still image camera and a continuous mode camera; analyzing said data based on said predetermined exposure settings, and determining a new exposure settings to the pulse (flash) light control and the continuous light control, thereby enabling to utilize the continuous light measured data to predict amount of light exposure to be used in the pulse (flash) light illumination.

BRIEF DESCRIPTION OF THE DRAWINGS

In order to understand the invention and to see how it may be carried out in practice, preferred embodiment will now be described, by way of non-limiting examples only, with reference to the accompanying drawings, in which:

FIGS. 5A and 5B exemplify a system of the invention utilizing a combination of LEDs of various operating wavelengths and a dichroic mirror;

FIG. 11 exemplifies an integrating sphere with a light-guide suitable to be used in the present invention;

FIG. 18A exemplifies a method of the invention used for controlling modification of different exposure parameters; and.

DETAILED DESCRIPTION OF EXEMPLARY EMBODIMENTS

Figure 1A:
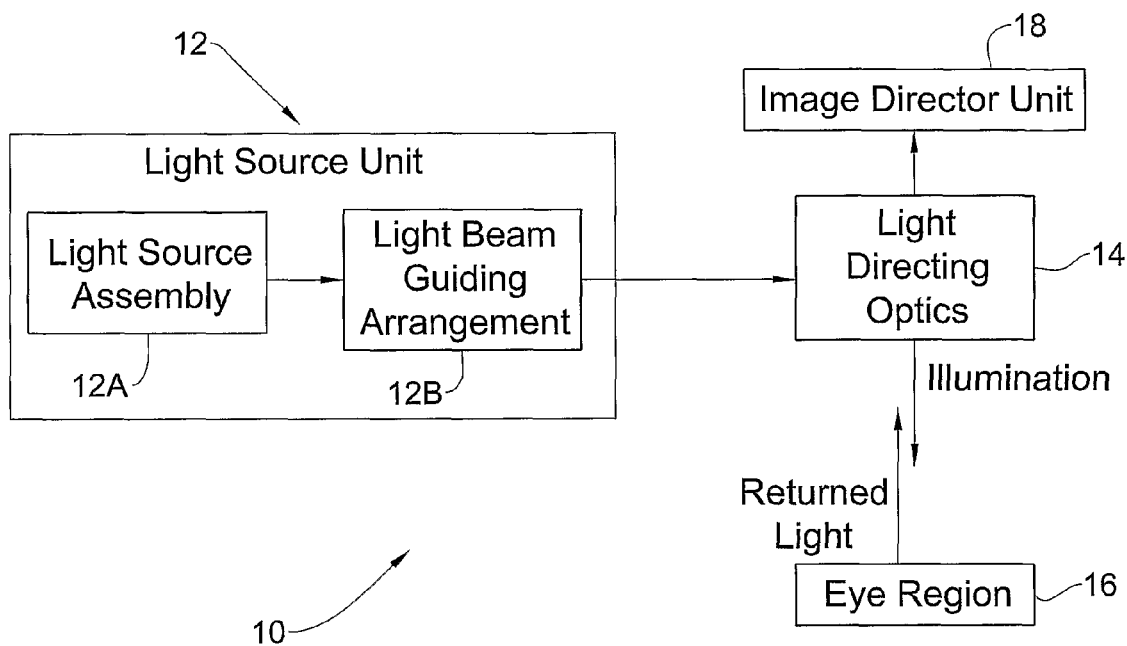
FIG. 1A is a block diagram of functional elements of a system (fundus camera) of the present invention.

Referring to FIG. 1A there is illustrated, by way of a block diagram, the main functional elements of a system 10 of the present invention suitable to be used in a fundus camera. System 10 includes a light source unit 12, including a light source assembly 12A formed by one or more LED-based units (each including a single LED or a LED-array) and a light beam guiding arrangement 12B. Also provided in system 10 is a light directing optics 14 and an image detector 18. System 10 is associated with a control system 19 configured for controlling various operational modes of system 10 as will be described more specifically further below.

Light beam guiding arrangement 12B is configured for coupling light from the LEDs and providing output light beam(s) of a desired shape. For example, the light guiding arrangement is configured to provide a ring-like shaped light output therefrom. It should be noted that the light beam guiding arrangement may be part of the light source assembly, or may be a separate assembly.

Light directing optics 14 includes lens arrangement (including an objective lens arrangement and an imaging lens arrangement) and a beam divider. Light directing optics 14 is configured and operable to collect and direct the ring-shaped illuminating light to an eye region 16 (constituting a region of interest), and collect and direct light returned (reflected and/or excited) from the illuminated eye fundus to an image detector 18.

Figure 1B:
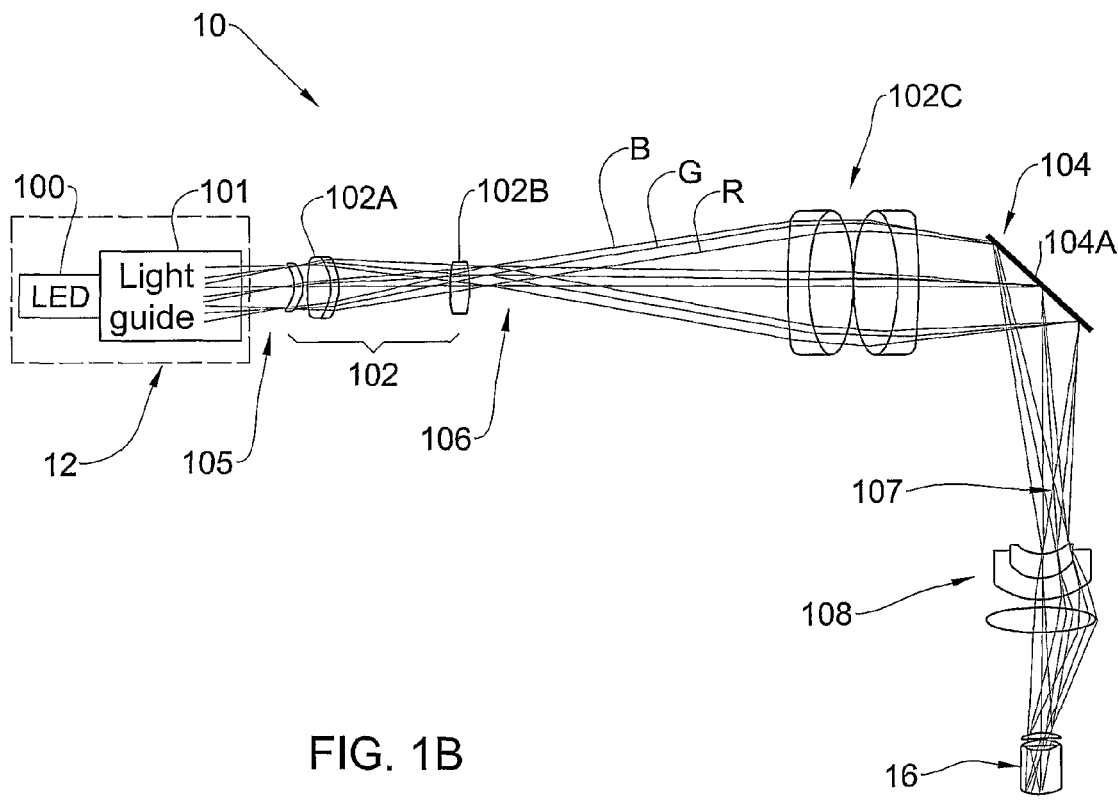
FIG. 1B is a schematic illustration of an example of the optical layout of an illumination channel of the system of FIG. 1A.

FIG. 1B illustrates a specific but not limiting example of the configuration of the above-described optical system layout 10. The system is designed to enable to meet the requirement of the high quality illumination of the eye fundus. System 10 includes a LED-based light source unit 12 including a light guide 101, a LED assembly 100 attached to one end of the light guide, and a lens arrangement 102 (presenting an entrance pupil 105) appropriately accommodated at the other end of light guide unit 101. Light guide unit 101 is configured as a cone-like reflector as will be exemplified further below with reference to FIGS. 12A-12B. In the present example, LED assembly is configured to generate light of Red (R), Green (G), Blue (B) (or preferably Cyan as will be described further below) and White colors. It should, however, be noted that the invention is not limited to the use of these colors and can be employed with less or additional colors as required by a specific application.

The LEDs illumination is usually not homogeneous, both spatially and angularly. Also, light emitted by LEDs is spread over large angles that may reach 180 degrees without passing through any lens arrangement. The system of the present invention is aimed at providing substantially homogeneous illumination of a region of interest (fundus) while utilizing such non-homogeneous illumination from the LEDs. To this end, light guide unit 101 is configured such that at the entrance pupil 105, the angle of a light beam emitted by the LED arrangement decreases into a cone of about 20 degrees or less. Namely, highly efficient light guide unit 101 collects large proportion of the light energy from the LEDs arrangement into such a beam cone.

Lens arrangement 102 includes a condenser lens 102A and a field lens 102B. The configuration and operation of such lenses are known per se and therefore need not be specifically described, except to note the following: A condenser lens is a large lens typically used in an optical projecting system to collect light, radiated from a light source, over a large solid angle and to direct this light onto an object (or transparency) that is to be focused at a certain distance by a projection lens. A field lens is typically placed in or near the plane of an image to ensure that the light to the outer parts of the image is directed into the subsequent lenses of the system and thus uniform illumination over the field of view is ensured. Lens arrangement 102 at the output of the light guide unit 101 thus creates another pupil which is the image of the exit pupil 105 at an interface plane 104 (where a combiner mirror 104A is located, being in the form of a mirror with a hole of a diameter that corresponds to that of the ring-like illumination, and also to the magnification factor of an objective lens arrangement). It should be noted that the term "hole" used herein signifies either an aperture (optical window) or a partially transmitting and reflective region. The latter allows for directing higher amount of energy towards the region of interest.

Lens arrangement 102 also includes a relay lens assembly 102C and an objective lens arrangement 108. Relay lens 102C is appropriately accommodated between field lens 102B and interface plane 104, and projects an intermediate image 106 onto an intermediate image plane 107 in front of objective lens arrangement 108. The latter focuses this image onto the region of interest 16 (fundus of the eye, represented here by an eye model).

Light returned from the illuminated region is collected by the same objective lens arrangement, passes through the hole (not shown here) in mirror 104A and then processed by an imaging optics (not shown here). Plane 104 serves as a common pupil for both the illumination and imaging channels, thus ensuring their full coherence and presenting the ideal interface between them. As indicated above, light combiner (mirror) 104A is placed in the reference plane 104, and is formed with a hole of a diameter that corresponds to the eye pupil size and the objective lens 108 magnification factor, such as to enable passage of the collected returned light (indicative of a retina image) therethrough and onto the imaging optics.

The above-described configuration of the illumination system ensures full coherence with imaging optics represented in the layout of FIG. 1B by the common objective lens arrangement 108. Also, this configuration ensures that the entire light produced by the LED arrangement enters the eye's pupil. This configuration and the use of LEDs lead to fundus illumination that is far more homogeneous both spatially and angularly then that used in the existing fundus cameras.

The following are various examples of implementing technique of the present invention, enabling the use of LED-based light sources in a fundus camera. To facilitate understanding, the same reference numbers are used for identifying those components that are common in all the examples of the invention.

Figure 2:
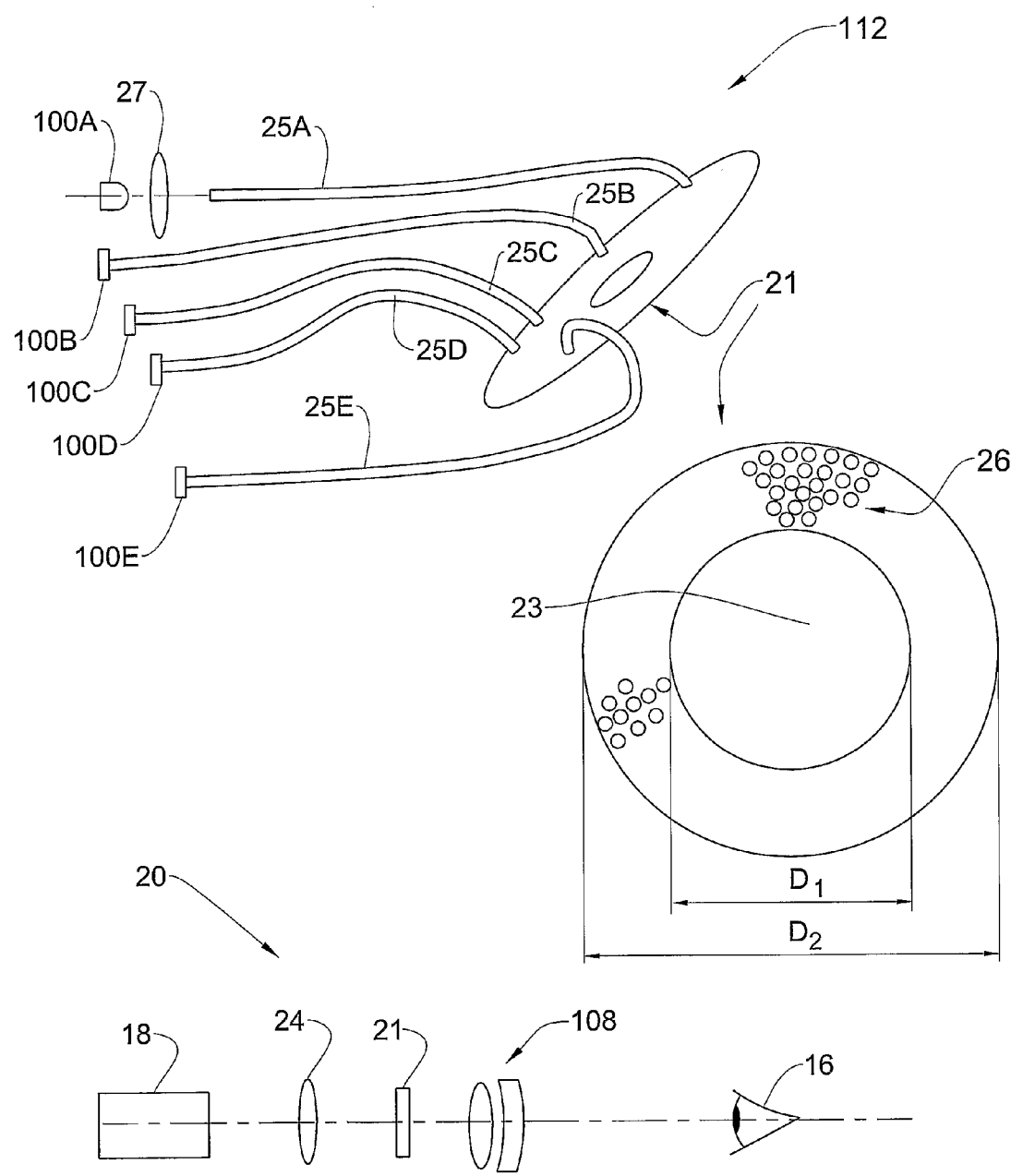
FIG. 2 exemplifies the configuration of a light source unit of the present invention configured to couple light from many LEDs through optical fibers which form a ring of light sources.

FIG. 2 exemplifies a light source unit 112 of the present invention configured to couple light from many LEDs into an optical fiber ring. FIG. 2 also shows an imaging channel 20 associated with such light source unit 112. In the example of FIG. 2, multiple LEDs 100A-100E are coupled to a fiber bundle defining a ring-like light output along a ring-like member 21 and an imaging path defined by an aperture 23 of this ring-like member. This technique allows for collecting light from a LED in a commercially available package (like SMT, TO—can or other package type), which is typically much larger than the active area of the LED-chip used for illumination, into a fiber with an active core of small dimensions.

As shown in the present example, light emitted by LED 100A is coupled to its associated fiber 25A via a lens 27, while the other LEDs 100B-100E are commercially available fiber-coupled LEDs. The opposite ends of all the fibers 25A-25E are arranged so as to define a ring-like light output 26. These fibers' ends are packed in ring 21 with certain inner and outer diameters $D_1$ and $D_2$. Light from ring 21 is imaged on the cornea of eye 16 via an objective lens arrangement 108. Inner diameter $D_1$ of ring 21 serves as aperture 23 for transmitting light. returned from the region of interest (fundus of the eye), via objective lens arrangement 108 and an imaging optics 24, to an image detector unit 18, which may be a CCD camera, eyepiece, film camera, LCD, etc. Preferably, the different wavelengths' channels (fibers) are arranged within the ring 21 such as to reach equal spectral distribution for as small as possible sub-section of the ring.

It should be noted although not specifically shown in the examples of the invention that imaging optics 24 may for example include focusing and relay lens arrangements. Preferably, according to the invention, image detector unit 18 includes two image detectors (live image camera and still camera), or preferably three image detectors (live image camera, still camera and monochrome camera, e.g., ICG-related camera) mounted such that at least some of them are selectively brought to the operational mode. In this case, imaging optics 24 preferably includes relay lens assembly for each camera, as well as a common relay lens assembly, and a common focusing lens arrangement.

The multiple LEDs' emitting light of different wavelength ranges can be used, for example Red, Blue, Green, White, and NIR, etc., and can be lit for each operation mode of the fundus camera. The operational include inter alia the following: FA, ICG, Red-free (Green), Red, Blue and Color Photography, as well as pulse (single pulse or pulse train) and/or continuous illumination. The inventors have found that for the FA, the use of exciting light of Cyan color and preferably within a specific wavelength range of 485 nm-500 nm, provides the optimal excitation of fluorescein.

Turning back to FIG. 2, the use of multiple fibers allows for enhancing the brightness of illumination. The use of LEDs of different wavelengths allows for the ring operation in all the modes without the need for movement of any part. The latter significantly facilitates operation of a fundus camera, as well as reduces the cost involved by adding a motor to move parts electronically.

It should also be noted that such a multiple-fiber coupler for the multiple LEDs eliminates the need for any beam combiner (mirror with hole) for combining the illumination and imaging channels; and the ring aperture can be used for the imaging path. Also, it should be noted that the above-described technique provides for coupling each LED to its associated fiber (rather than coupling a large LED or a LED-array to a fiber bundle consisting of a number of single fibers). As a result, the dead-area around each LED does not reduce the brightness. A cost effective option to implement this is by arranging the discrete LEDs in a matrix and coupling them with a lenslet array to a matrix of fibers, where each lens element of the lenslet array is dedicated to couple one LED to one specific fiber bundle.

Figure 3:
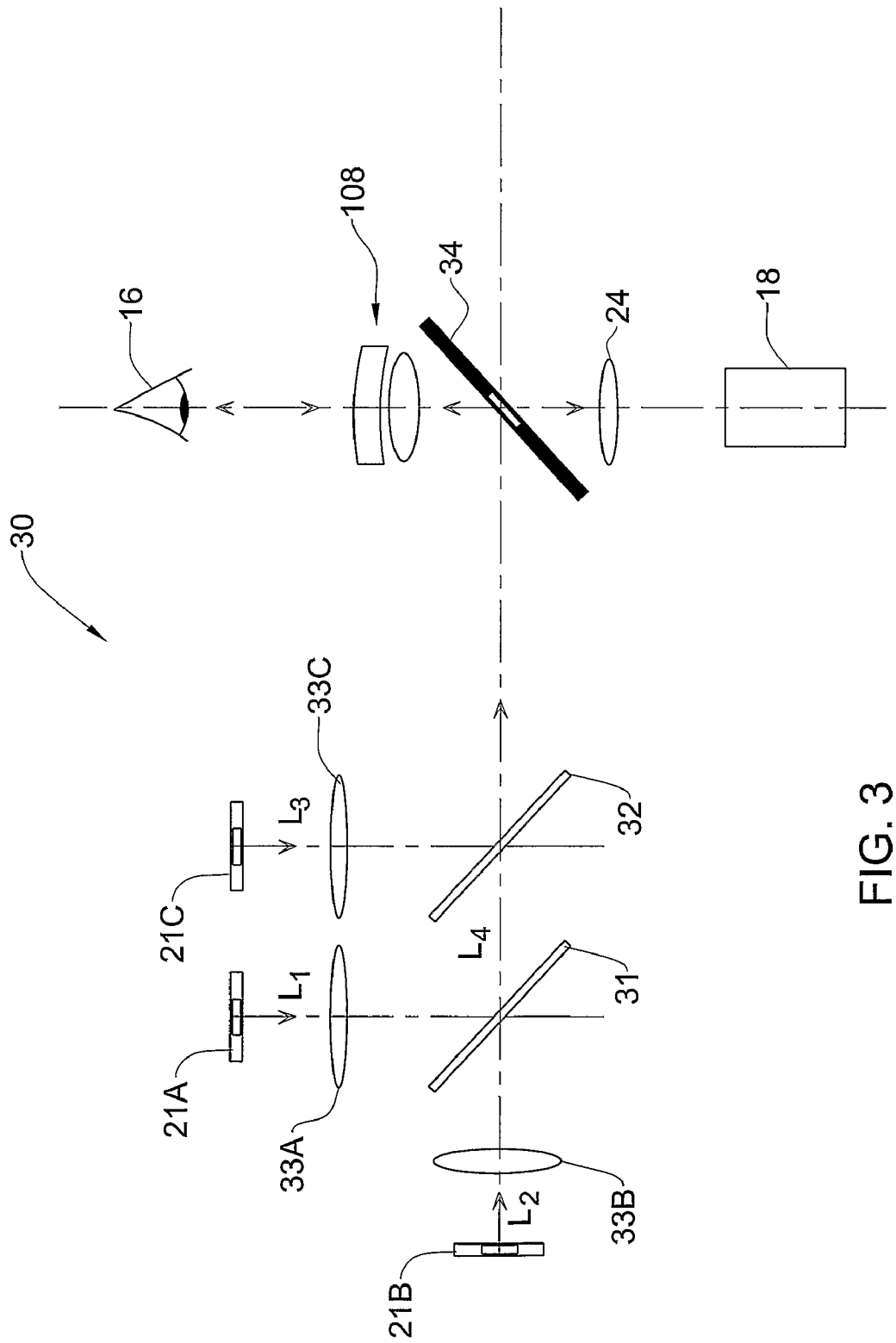
FIG. 3 exemplifies an imaging system (fundus camera) of the present invention utilizing coupling of many fibers into several rings.

FIG. 3 illustrates an imaging system 30 (fundus camera) of the present invention utilizing coupling of many fibers into several rings. This technique provides for achieving higher brightness than that obtainable with the configuration of FIG. 2, and utilizes a dichroic mirror for combining rings from various wavelengths. This provides a larger active area of the fibers dedicated for each wavelength channel, and thus more illumination power for each operational mode. This creates a larger set-up, and significantly higher illuminating power.

System 30 includes a light source unit formed by several fiber coupling rings (constituting LED assemblies with their associated light beam shaping assemblies), three such rings 21A, 21B and 21C in the present example; wavelength-selective splitter/combiners (dichroic mirror) 31 and 32, and condenser lenses 33A-33C associated with rings 21A-21C, respectively. Light portions $L_1$ and $L_2$ from rings 21A and 21B, respectively, are combined by dichroic mirror 31, which transmits light in a spectral range of 750-800 nm and is highly reflective to a 400-700 nm spectral range. The so-produced combined light beam $L_4$ is then coupled with a light portion $L_3$ from ring 21C, by dichroic mirror 32, which is highly reflective and transmitting for wavelengths, respectively, below and above 500 nm.

This technique is thus generally similar to that of FIG. 2, but concentrates light of one or more wavelengths (each wavelength corresponding to a specific mode of operation) in a special ring. More specifically, Blue or Cyan LED for FA is concentrated into ring-like light source 21C, a white or RGB light—into ring-like light source 21A, and 790 nm light for ICG or NIR illumination—into ring-like light source 21B. This also allows for creating a white or RGB color ring by combining the RGB ring, in which blue color is typically of relatively low power thus presenting the so-called "white minus blue" ring at high power, with a separate high-power blue LED. Hence, blue color can be enhanced by utilizing the additional blue LED. More specifically, this is achieved by lighting white (RGB) ring 21A with higher intensity and lighting blue ring 21C (even with lower intensity) thus forming a controlling tool of the white light spectrum and intensity.

As further shown in FIG. 3, light portions $L_1 \div L_3$ of rings 21A-21C are imaged via lenses 33A-33C, respectively, on a combiner 34. Here, the light is re-imaged via an objective lens arrangement 108 on the region of interest (fundus) 16. Light reflected or excited (fluoresced) from the fundus of the eye is imaged via objective 108 and an imaging optics 24 onto an image detector 18.

Figure 4:
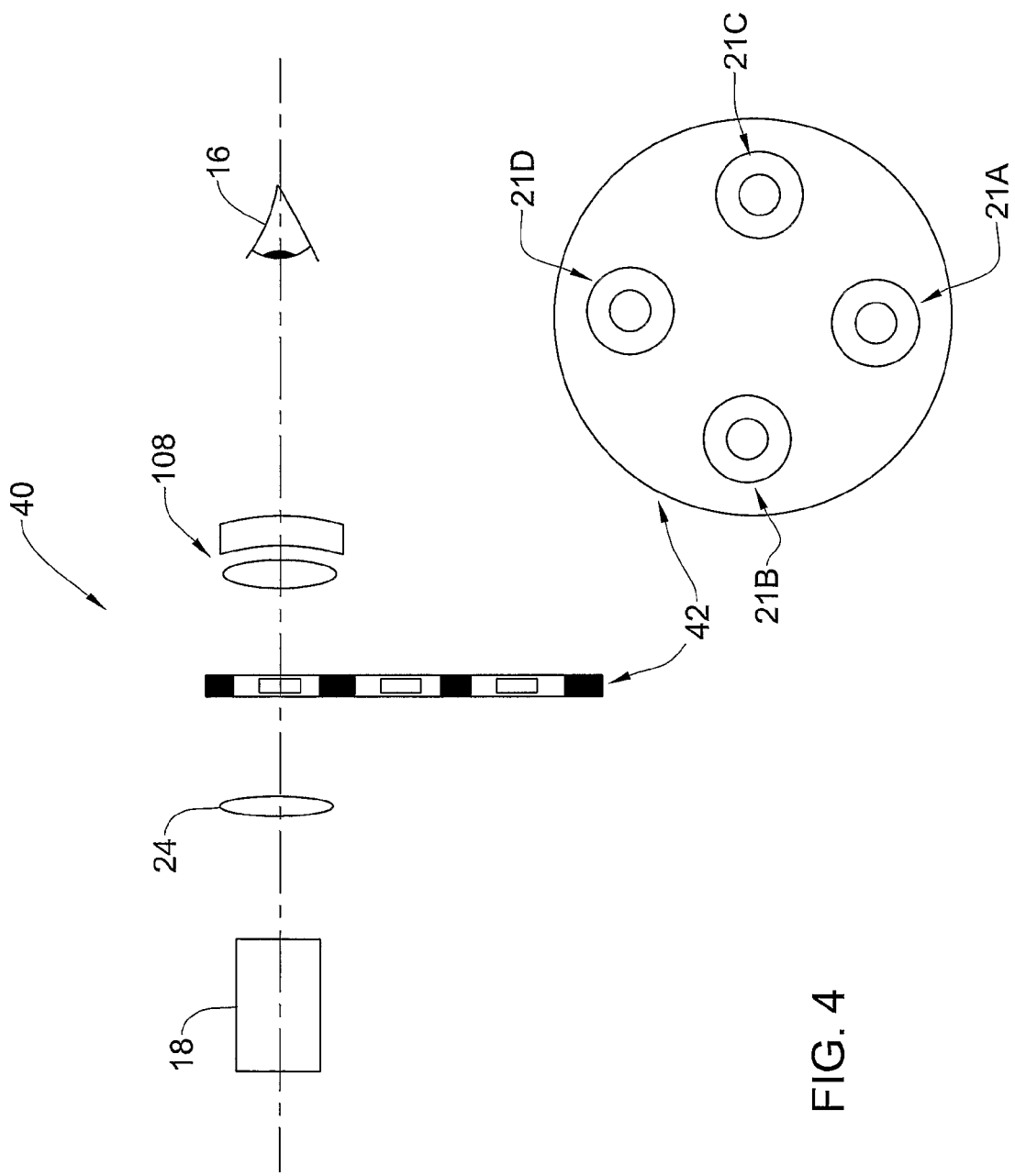
FIG. 4 exemplifies a system of the present invention utilizing mechanically exchangeable rings.

FIG. 4 exemplifies a system 40 of the present invention utilizing mechanically exchangeable rings. This configuration, although requiring the ring movement for changing the operational mode of the system, provides for even higher brightness, since it does not need any beam splitters that absorb part of the energy transmitted through (or reflected from) them.

System 40 includes a light beam shaping arrangement in the form of light collecting rings 21A, 21B and 21C (similar to the above-described system 30), each corresponding to a specific illumination mode (such as FA, ICG, etc.). These rings are located on a wheel 42, which is driven for rotation, and optionally contains an additional ring (to form an additional ring-like light source) 21D. To select for operation a certain illumination mode, wheel 42 is rotated to a position thereof to locate the operative one of the rings 21A-21D between an imaging optics 24 and an objective lens arrangement 108. Hence, the active ring operates as described above with reference to FIG. 2. Rotation of the wheel 42 sequentially brings one of rings 21A-21D to its operative (active) position.

Reference is made to FIGS. 5A and 5B showing a system 50 of yet another example of the invention utilizing a combination of LEDs of various operating wavelengths and a dichroic mirror. This configuration achieves higher brightness and allows for operating a white source by combining a blue source at low power with a "white minus blue source" at higher power. In this configuration, the optics are inexpensive, straight-forward and easy to design.

As shown in FIG. 5A, light from a LED or LED-array 100A is focused by a lens 33A, and optionally further passes through a filter 52A, onto a plane where a ring-shaped mask assembly 54 is located. This mask assembly can include a set of different masks (different patterns), e.g., having different inner and/or outer diameters. As exemplified in FIG. 5B, this may be spaced-apart differently patterned regions 54A and 54B of a common substrate 55: region 54A acts as a mask with inner and outer diameters 56A and 56A', and region 54B that acts as a mask with inner and outer diameters 56B and 56B'.

By displacing substrate 55 with respect to the light propagation path, a different mask (one of regions 54A and 54B) is brought to an operative position, i.e., affects the light by applying beam shaping thereto. Substrate 55 may be glass or other optically transparent material, patterned by chrome or other non transparent coating, thereby defining a mask in the form of a pattern of light transmitting and blocking regions.

A light portion $L_1$ emitted by LED or LED-array 100A (being a Blue LED) is combined with a light portion $L_2$ from LED or LED-array 100B (being RGB/White light) by a dichroic mirror 31; and is further combined with a light portion $L_3$ from a light source 100C (NIR spectrum) via a dichroic mirror 32. Light source 100C may be LED or laser diode. It should be noted that light source 100B is positioned upstream (with respect to the light propagation towards an eye) of mask 54 and a mirror 34 (mirror with hole). The illuminating light therefore cannot shine in full brightness in the eye, and damage threshold will not be reached. The advantage of using a laser diode is its high brightness (typically higher than that of LED). If the white LED based channel 100B cannot operate the R, G and B colors separately, a frequency selective filter unit (filter wheel) 52B containing R, G and B filters is used, being accommodated in the optical path of light emerging from light source 100B. The ring-form light from mask 54 is imaged via an imaging lens arrangement 57 onto the reflective surface of mirror 34. Further propagation scheme of the illuminating light, as well as that of the returned light, is similar to that described above with reference to FIG. 3.

Figure 6A:
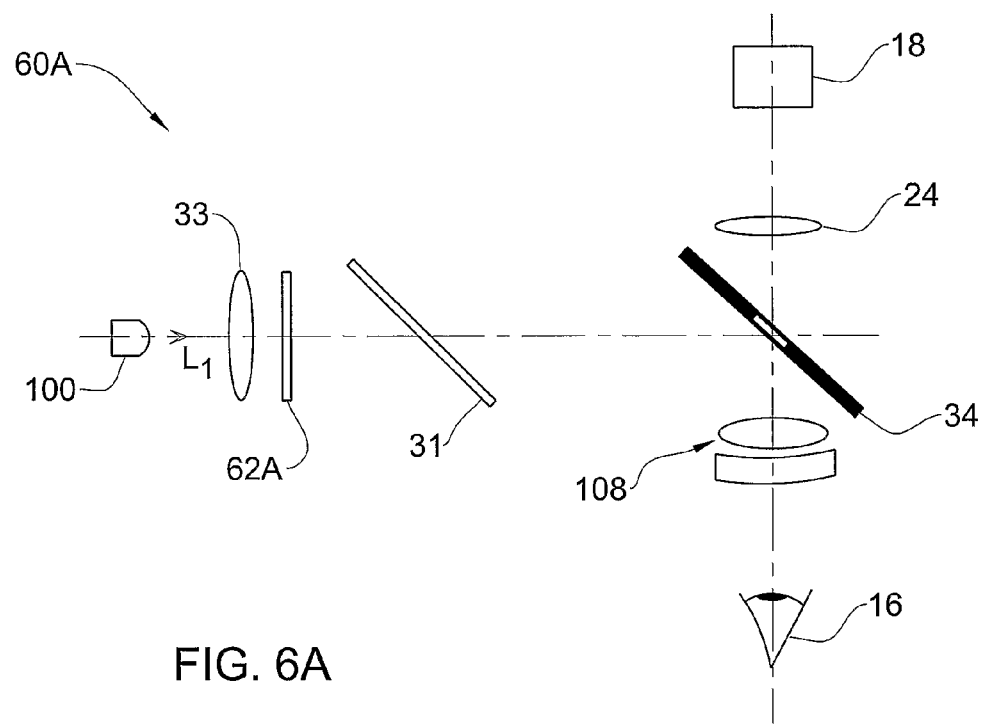
FIGS. 6A and 6B exemplify illumination systems utilizing diffractive and refractive optics, respectively.
Figure 6B:
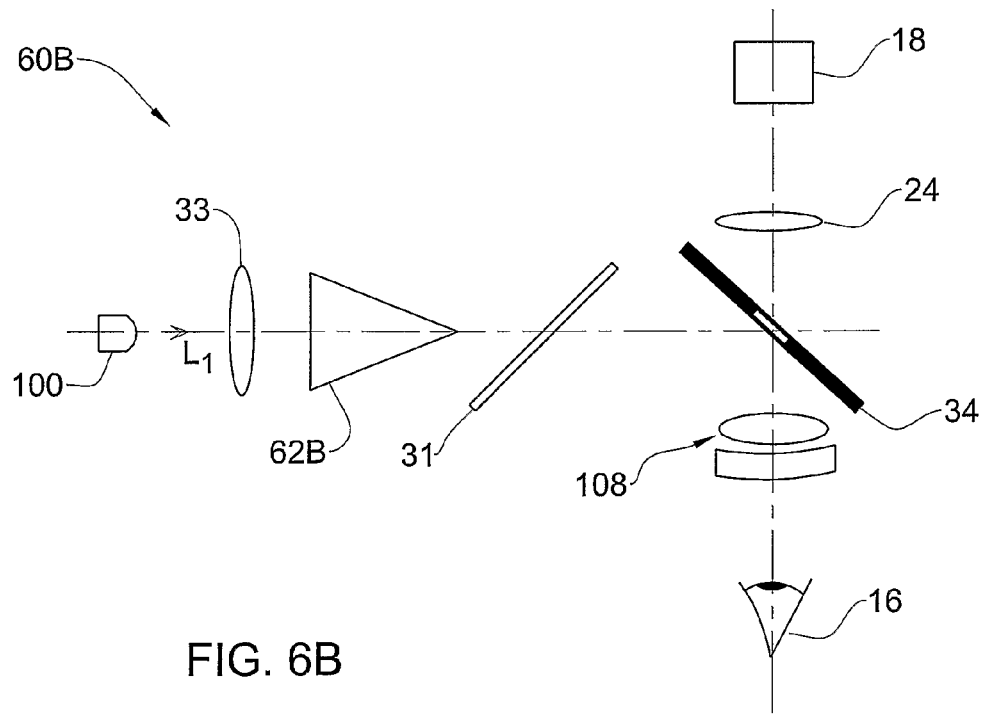

FIGS. 6A and 6B exemplify illumination systems 60A and 60B utilizing diffractive and refractive optics, respectively.

System 60A uses a diffractive element 62A for high efficient coupling of Lambertian light into a ring. Such a diffractive element may be diffractive axicon or diffractive-type micro-prism array. The use of diffractive axicon element provides close to 100% coupling of light in case the incoming light is collimated. To this end, the light source unit preferably includes LEDs.

Light $L_1$ (Blue or Cyan) from a LED or LED array 100 is collimated by optics 33 and is projected via diffractive element (axicon or prism array) 62A on a combining mirror with a hole 34. Other light channel(s), if used, may be combined via one or more dichroic mirrors as described above (single such mirror 31 being shown in the present example). The illuminating light continues its propagation to an eye 16, and returned light is directed to an image detector 18 as described above.

System 60B is similar to the above-described system 60A, but uses a refractive optical element 62B for high efficient coupling of Lambertian light into a ring. Refractive optical element 62B is either refractive axicon or refractive-type prism array. The refractive axicon, although being larger and possibly more expensive when replicated in high volume, requires less tooling charge and is less wavelength-dependent than the diffractive alternative.

It should be noted that the diffraction/refraction of a micro-prism array can be optimized, such that light at each position on the array is diffracted/refracted in a way optimal for that position. It should also be noted that it is relatively easy to manufacture a refractive micro-prism array of large refraction angles, typically larger than the angles achievable with a diffractive micro-prism array.

Figure 7:
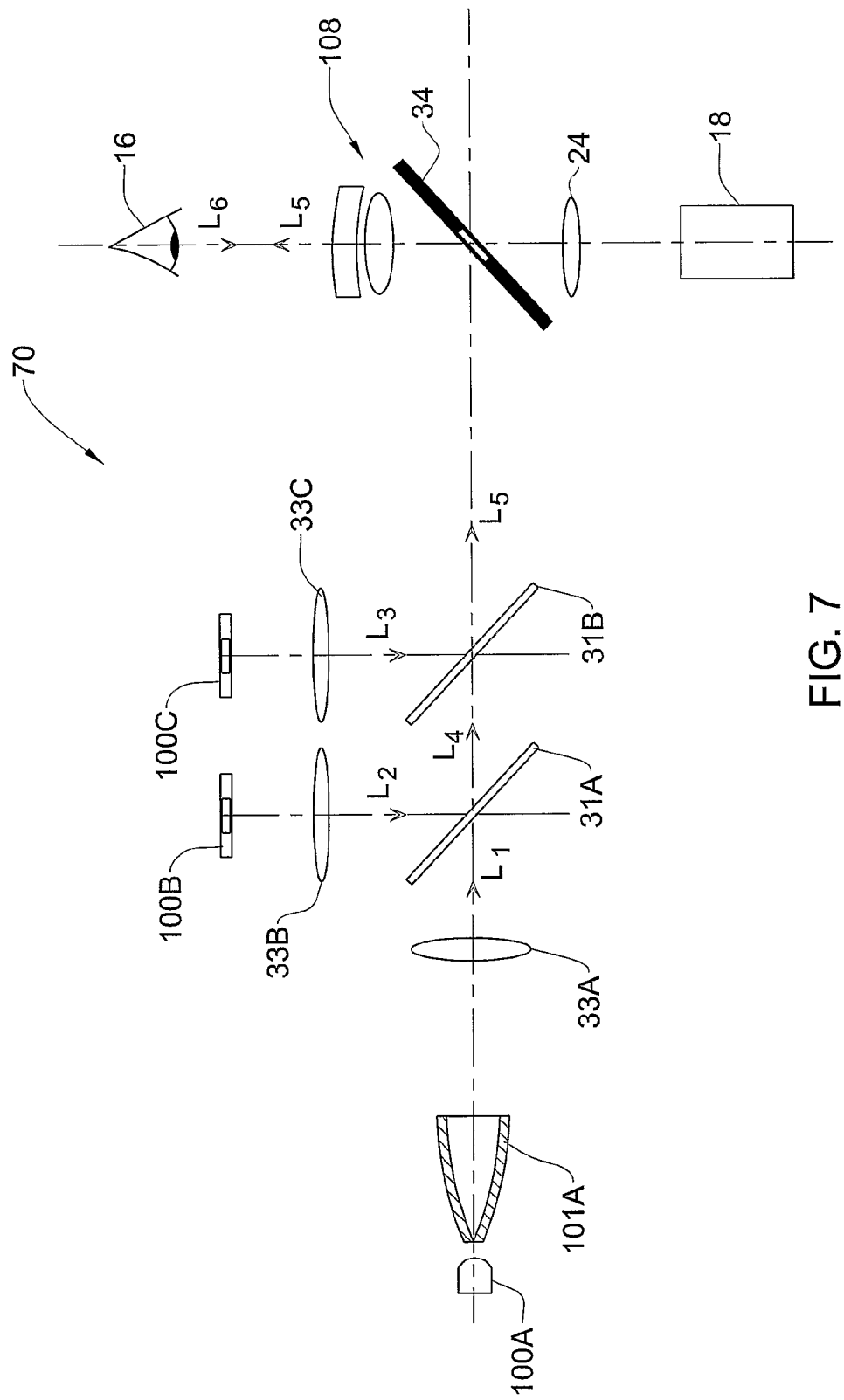
FIG. 7 exemplifies a system of the present invention utilizing a light beam shaping arrangement configured for guiding light from a LED towards a region of interest.

Reference is made to FIG. 7 exemplifying an optical system 70 utilizing a light beam shaping arrangement in the form of a light guide for guiding light from a LED towards a region of interest. This technique provides for coupling light of a LED, emitting light at a large angle, by a light guide that guides this light into a small ring or into a predetermined beam cone. The ring can be enlarged to reach the required dimensions on a combining mirror (mirror with hole) and decrease the angle of the light cone accordingly. This advantageously allows for collecting light from the guide in large angles by an objective lens arrangement that is by itself capable of collecting light impinging thereon in a small cone.

System 70 includes a LED assembly 100A (single LED or LED array); a light guide 101A configured to provide, from light emitted by the LED arrangement, ring-like illumination at the output of the light guide; a lens arrangement 33A for imaging light emerging from the light guide onto a combining mirror 34. As also shown in the figure, the system may include several additional LEDs assemblies with their associated light guiding units and optics. More specifically, in the present example, the LEDs arrangement includes three LED assemblies 100A, 100B and 100C, associated with three light guides, respectively (only one such light guide 101A being shown in the figure), and three lens arrangements 33A-33C. Dichroic mirrors are appropriately provided: dichroic mirror 31A combines light portions $L_1$ and $L_2$ from LEDs 100A and 100B producing a combined light beam $L_4$; and dichroic mirror 31B combines this combined light beam $L_4$ and light $L_3$ from LED 100C into a further combined light beam $L_5$. The latter is directed by mirror 34 towards an eye 16 via an objective lens arrangement 108. Light $L_6$ returned from the illuminated region in the retina (and indicative of the image of the illuminated region) is collected by objective 108 and transmitted by mirror 34 towards an imaging lens 24 which relays the image onto an image detector 18.

Figures 8A, 8B:
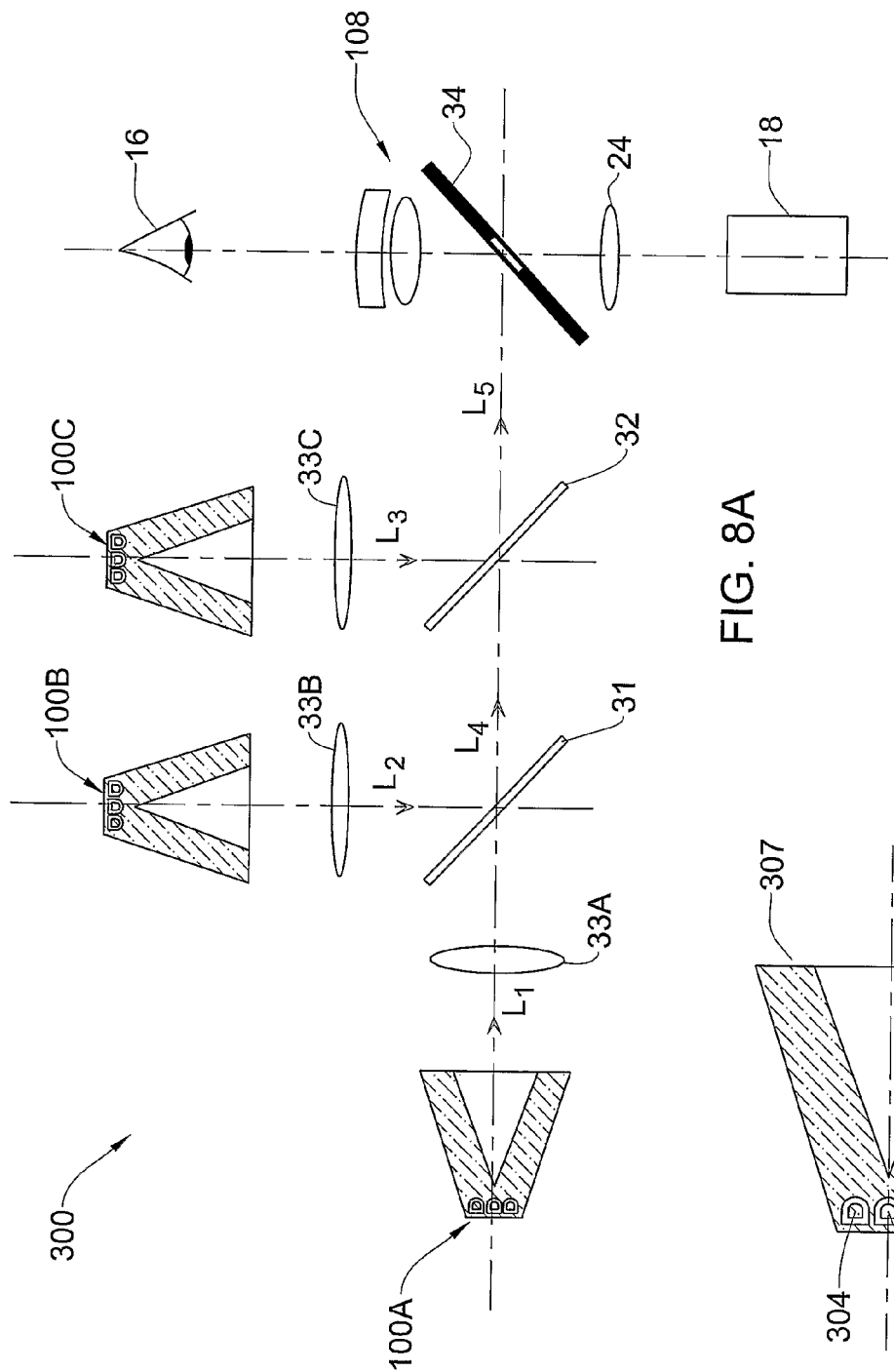
FIGS. 8A and 8B exemplify a system of the invention utilizing several light guides of similar design for several LEDs.

Reference is made to FIGS. 8A and 8B exemplifying a system 300 of the invention utilizing a common light guide for several LEDs. This technique provides for coupling light from a number of LEDs into a single light guide that collects all the light into a single ring.

As shown in FIG. 8A, system 300 includes a LED arrangement formed by several LEDs assemblies 100A, 100B and 100C; and an optical system including condenser lens arrangements 33A-33C associated with LEDs assemblies 100A-100C, dichroic mirrors 31A and 31B operating together to combine light portions $L_1 \div L_3$ from the LEDs assemblies; a combining mirror (mirror with hole) 34; and objective and imaging lens arrangements 108 and 24. As shown in FIG. 8B, the LEDs assembly (assembly 100A being shown in the figure) includes LEDs 302 and 304 associated with a common light guide 306. Light from LEDs 302 and 304 is guided to a ring-like form at the output 307 of the light guide 306. Optionally, an inner surface 308 of the light guide is coated with glossy or diffusive reflective material, such as Silver, Aluminum, to enhance the illumination efficiency. The light guide body 306 may be made of PMMA or other plastic or glass material.

It should be understood that the use of additional LEDs assemblies (100B and 100C) with their associated optics is optional. The system may utilize either one large light guide containing LEDs of all the colors, or couple them with other channels via dichroic mirrors as shown in FIG. 8A. Light guide 306 can either encapsulate the LEDs to reach higher efficiency as shown, or circumvent the LEDs as is common practice in the art (not shown).

The above-described technique uses light from more than one LED and can reach therefore higher brightness, although it requires a more complex light guide than that described above with reference to FIGS. 8A-8B.

Figure 9:
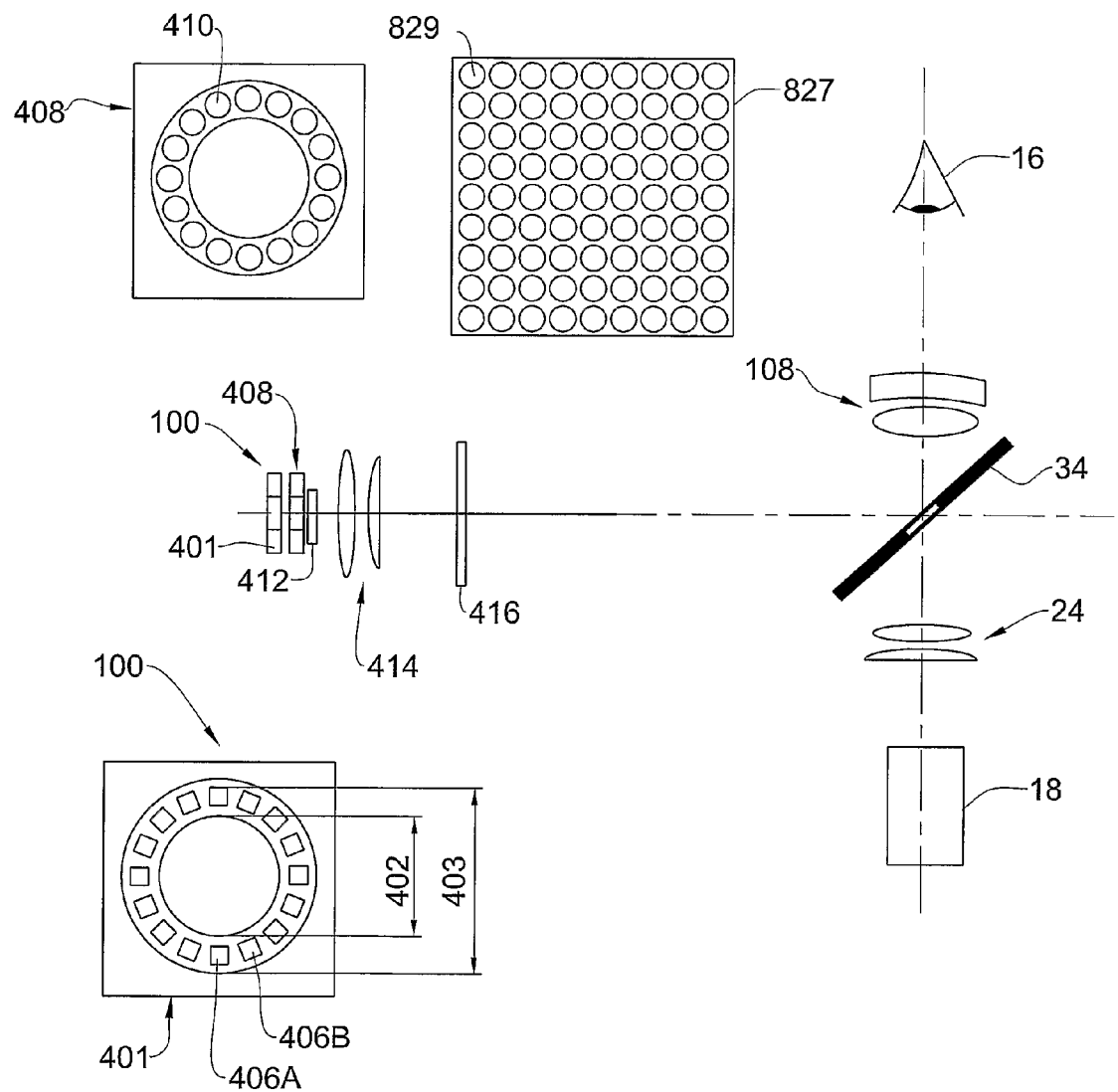
FIG. 9 exemplifies the configuration of a LED arrangement with a ring-like shape topology of LEDs suitable to be used in the present invention to increase the system efficiency.

Reference is made to FIG. 9 exemplifying the configuration of a LED arrangement suitable to be used in the system of the invention. This technique utilizes the topology of LEDs in a ring-like shape to increase the efficiency. Here, a system 400 is shown configured generally similar to the above-described examples, namely including a LED arrangement 100, an annular mirror 34, an objective lens arrangement 108, and an imaging optics 24.

In the present example, LED arrangement 100 is in the form of a ring-like shaped structure 401 containing LEDs within its borders of an inner diameter 402 and an outer diameter 403, thus creating a ring-like shaped light source formed by a number of LEDs arranged in a circular array. Optionally, locally adjacent LEDs 406A and 406B contained in the array have different emitting spectra and/or power, or the LEDs array contains different groups of LEDs, each group having about the same spectrum and/or power. Each type of LED can be of a spectrum optimized for a specific operational mode, like FA or ICG. It should be noted, although not specifically shown, that several such rings 401 can be combined by dichroic mirror(s) as described above, to make an overall brighter ring that has a more uniform spectral and/or power distribution.

Also, optionally, at least some of the LED's can be associated with a condensing element to narrow the emitting angle and/or associated with a diffusing element to make the source more uniform. Additionally or alternatively, one or more micro lens arrays 408 may be used to condense and/or diffuse light emitted by some or all of the LEDs in the array. The micro lens array 408 may be put close to the ring 401 and designed such that each lens element 410 is optimized to collect light from one LED chip; and/or another micro lens array 412 may be placed a bit further away and having lens elements optimized to collect light from the obtained light distribution in the plain it is positioned.

Light emerging from the lens array(s) can optionally be further condensed and/or imaged by lens assembly 414, and may or may not then pass through an optical filter or filter-set 416 to narrow the spectrum of light. Ring 401 will be further imaged on mirror 34 and via objective lens assembly 108 on eye 16. The reflecting or fluorescing light from the eye 109 is imaged by objective lens assembly 108, onto mirror 34, and then re-imaged by ocular lens assembly 24 on an image detector 18 (which may be a CCD camera, eye-piece or similar target).

Figure 10:
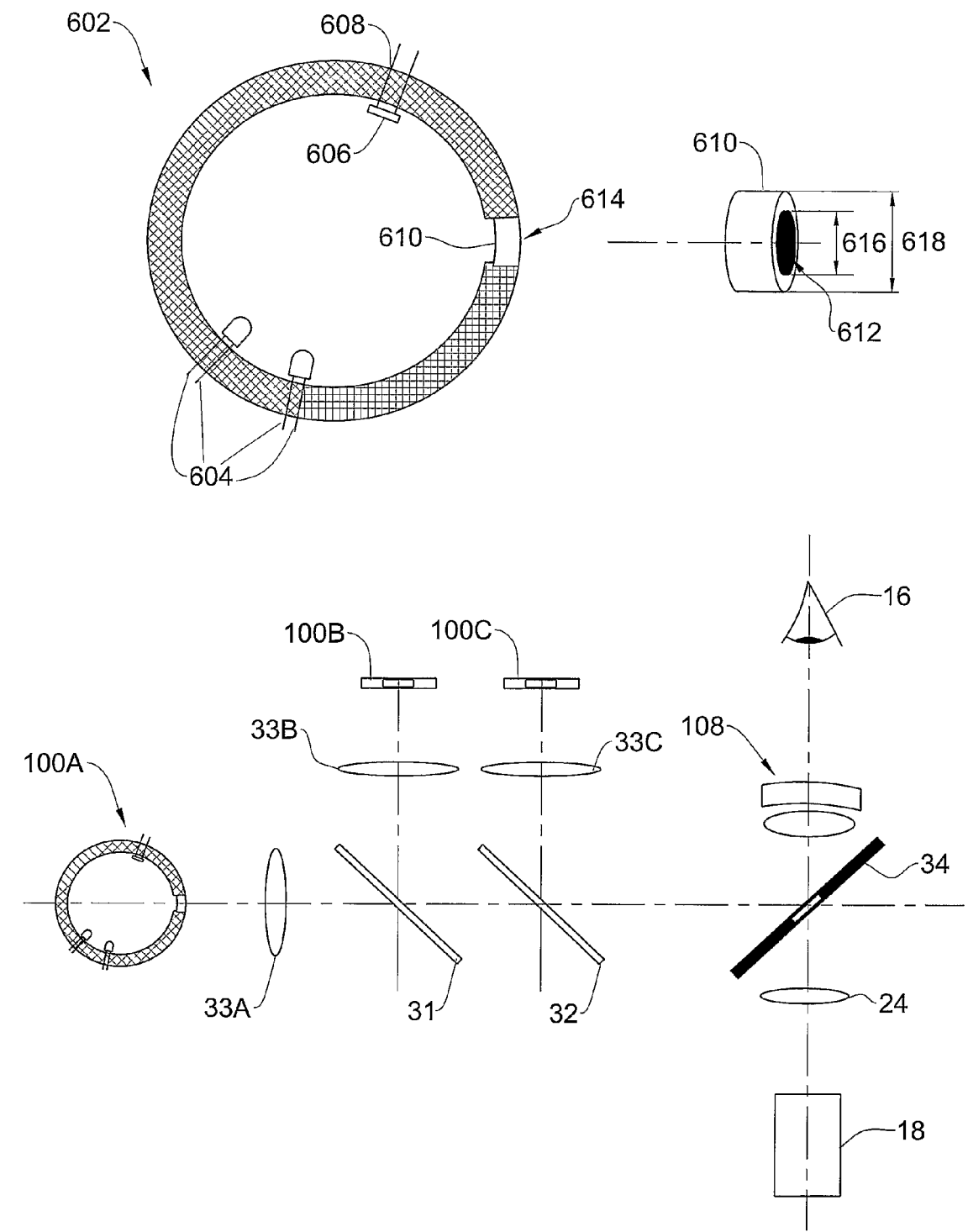
FIG. 10 exemplifies a system of the present invention utilizing an integrating sphere as a light source.

FIG. 10 exemplifies an optical system 600 utilizing an integrating sphere. According to this technique, light that does not emerge from a ring is recycled by internal reflection in the integrating sphere and has a large probability to exit the sphere at the ring after one or more reflections in the integrating sphere. This enables to reach a higher coupling efficiency. System 600 includes a LED arrangement formed by a single LED assembly 100A and its associated light directing optics (condenser 33, mirror with hole 34, objective lens 108, imaging lens 24), or also including one or more additional LED assemblies (two such assemblies 100B and 100C being shown in the present example) in which case dichroic mirror 31 and 32 are appropriately provided for combining light from all the LED assemblies and directing combined light to mirror 34.

The LED assembly is formed by an integrating sphere or chamber 602 in which LEDs or LED arrays are mounted: the legs of LEDs pass through holes 604 to the outside where they can be connected to a current source (not shown). Another option to connect LEDs or LED arrays 606 to the wall on position where the wall consists locally of conductive material 608, or yet another option is used where the LED's are mounted in the sphere (not shown). Light emitted from the LED can bounce many times against the highly reflective holes and leave via a window 610. An inner ring 612 of the window can be coated with a reflective material, or an external mask 614 can be positioned to cover the inner diameter of the window, creating a ring-like shaped light-source with inner and outer diameters 616 and 618. The wide angle of radiation coming out of the window 610 can be narrowed by optics 33A (or 33B, 33C) that enlarges the size of the ring on mirror 34 and narrows its radiation angle. The integrating sphere can contain light from all channels, or the channels can be combined via dichroic mirrors 31 and 32 as described above.

FIG. 11 exemplifies an integrated sphere with a light-guide suitable to be used in the present invention. According to this example, light from a sphere configured as described above is guided via a light-guide, aimed at narrowing the exit angles of the ring and matching them with those that can be accepted by the objective. More specifically, inside an integrating sphere or chamber 702 LEDs or LED arrays are placed with their legs passing through holes 604 to the outside where they can be connected to a current source (not shown); or LEDs or LED arrays 606 are connected on the wall on position where the wall consists locally of conductive material 608; or the LEDs are mounted in the sphere (not shown). The emitted light can bounce many times against the highly reflective holes and leave via a window 710 or an open space. The window can be coated with reflective material creating a ring form aperture with inner diameter 716 and outer diameter 718.

The wide angle of radiation coming out of the window 710 can be narrowed by placing a light guide 720 after this aperture that guides the light from a narrow circle aperture with inner diameter 722 and outer diameter 724, to a wider ring with an inner diameter 722' and an outer diameter 724'. The light guide 720 is designed such that at its output side light exits in a ring-like shape and has a narrow divergent angle. To enable modification of the inner and outer diameters of the ring needed for myd versus non-myd or large versus small pupil exposures, the inner and outer diameter of the exit ring can optionally be resized by placing a mask 730 at its output side that hinders light, outside its outer diameter 732 and outside its inner diameter 734, to pass therethrough. This mask can be removed or moved and replaced by another mask or a transparent window 740 that will allow the entire ring-shaped light from the light guide to pass therethrough. The non-transparent part of the mask can optionally be reflective, so that light reflected to the light guide and/or sphere can arrive within the desired ring-like shape after one or more reflections.

As assembly 750 formed by integrating sphere 702 with light guide 720 can contain light from all channels or the channels can be combined via dichroic mirrors as described above. Alternatively, a light guide can be designed so as to contain a part like the sphere described above with reference to FIGS. 8A-8B, and a part like the light guide described below.

Figure 12A:
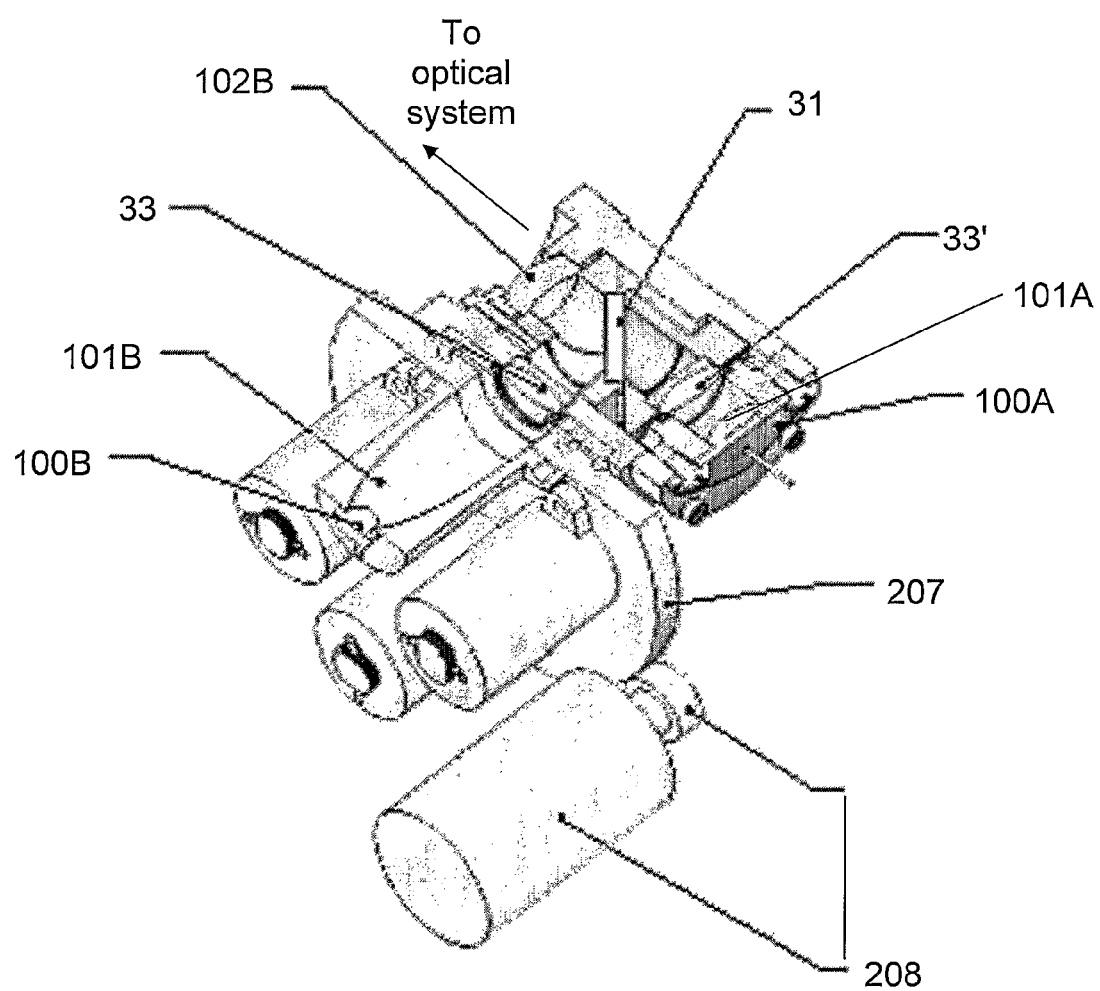
FIGS. 12A and 12B exemplify an optical device configured as an "adaptor" unit for use with a LED arrangement in the system of the present invention.
Figure 12B:
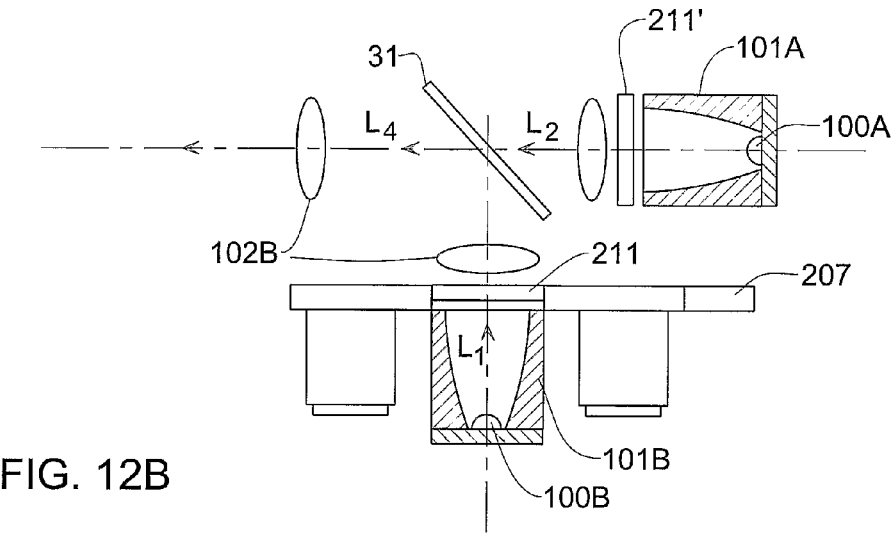

Reference is now made to FIGS. 12A and 12B exemplifying an optical device configured as a so-called "adaptor" unit 200 for use with a LED to arrangement in the system of the present invention.

Optical device 200 is formed by a light guide 101 and its associated optics. Device 200 includes a lens arrangement formed by a condenser lens 33 and an additional identical condenser lens 33'; and a dichroic mirror 31 inclined at 45 degrees with respect to a light path. A LED arrangement 100 includes two types of LEDs (or LEDs arrays): LED 100A emitting light at about 760-800 nm (NIR LED) and "visible" LEDs 100B. Each LED is assembled on a light guide configured as a cone-like reflector (e.g., a "Compound Parabolic Concentrator"—CPC). Such a light guide unit is a hollow cone-like member with its inner surface reflective with respect to a wavelength range emitted by a LED arrangement to be used with this light guide unit. Generally speaking, the geometry of such a reflective light guide unit (i.e., its inner diameter function and its length) defines the output light beam characteristics (e.g., homogeneity and divergence angle). The light guide unit is permanently attached to a LED selection unit (e.g., wheel 207) such that the light exit of the light guide unit is located at the entrance pupil of unit 200, and is designed to fit a LED mounted on its other end in order to optimize the efficiency of light collection. As shown in FIG. 12B, LED(s) 100A is associated with CPC 101A, and LED(s) 100B is associated with CPC 101B.

Unit 200 is configured to select one LED from a multiple "visible" LEDs for the operational mode of the system. In the present example four such visible LED units (LED with its light guide) are shown (FIG. 12A). In the present example, the selection of light source (LED) is realized by using a wheel (gear driven) 207 that is motorized by a motor and gear arrangement 208. The LED selection is controlled through a control unit and a digital interface on a controlling electronic circuit (which are not shown here). A common field lens 102B is assembled at the third portion (exit) of unit 200 through which an illumination beam is directed into an optical system (described above) that directs the illumination beam towards the eye fundus through an objective lens arrangement (not shown here).

The selectable LEDs are all in the visible range. Therefore, dichroic mirror 31 reflects this visible light from LEDs 100B and transmits light from the NIR LED 100A. The selectable light sources contain at least white, blue, green, red LED sources.

The optical scheme of unit 200 is illustrated more specifically in FIG. 12B. As shown, visible LEDs' units (three of them being seen in the figure) are mounted on rotatable wheel 207. Light $L_1$ from LED 100B is guided through CPC (reflector) 101B towards condenser lens 33 (optionally through an FA excitation filter 211) and further towards dichroic mirror 31. NIR light $L_2$ from LED 100A is guided through its associated CPC 101A to condenser lens 33' (optionally through an ICG excitation filter 211') which directs this light onto dichroic mirror 31. The latter combines light portions $L_1$ and $L_2$, and combined light $L_4$ is collected by common field lens 102B.

The above-described configuration, on the one hand, provides for aligning the NIR LED 100A illumination of the system (camera) to the patient's eye, thus enabling the so-called Non-Mydriatic mode (for non-dilated pupils), and also allows general use of the system without irritating the patient's eye with continuous visible light. On the other hand, the above configuration provides a fundus camera with the ICG option, where NIR LED 100A is being utilized as a flash LED at high intensity. The selectable light source stands-by for the flash illumination and photo—for all other procedures.

Where required, a bandpass or cut-off filter (excitation filter) 211 is incorporated as an integral part of each light source sub-assembly. Specifically, such filters are incorporated with the LED that illuminates light for the FA procedure, and with the NIR LED when used for the ICG procedure.

Figure 13:
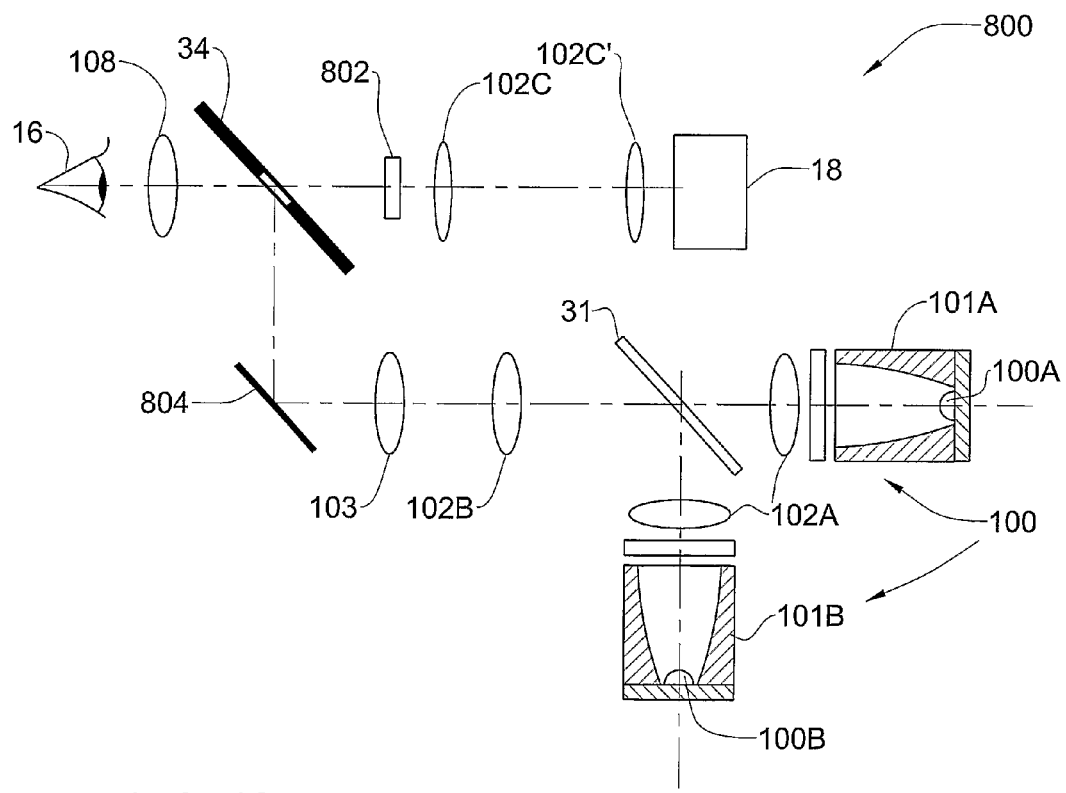
FIG. 13 exemplifies a system of the invention utilizing a spectral filter configured as a dual spectrum barrier filter.

According to some other aspects of the invention, it provides for fast and effective FA and ICG imaging in a concurrent or quasi-concurrent fashion. In this situation, a patient is injected with both ICG and fluorescein agents, and either concurrent or consecutive images will be acquired by operating the FA-wavelength LED in a flash mode and operating the ICG-wavelength LED in a flash mode, correspondingly. This feature of the invention provides for solving a long-felt need for ophthalmologists to diagnose simultaneously (in the same examination session) various pathologies in the retina. This feature can be achieved due to the use of a novel design of the above-described adaptor unit 200 (needing no moving parts during the session, i.e., upon selecting desired LED units) and by incorporating therein a novel filter assembly. In this connection, reference is made to FIG. 13 exemplifying an optical system 800 of the invention utilizing a spectral filter (preferably configured as a dual spectrum barrier filter) 802.

System 800 includes a LED arrangement 100 with its associated optics directing light towards an annular mirror 34, an objective lens arrangement 108 in the optical path of incident and returned light, and an imaging channel formed by mirror 34, imaging optics including first and second relay optics 102C and 102C', and a spectral filter 802. LED arrangement 100 includes a NIR LED unit including a NIR LED (or LED array) 100A and its light guide (CPC) 101A, and a visible LED unit including a visible LED (or LED array) 100B and its light guide (CPC) 101B. A dichroic mirror 31 combines light from LEDs 100A and 100B and directs combined light towards a field lens 102B, and a relay lens 103, and then onto a mirror 804 which reflects this light onto annular mirror 34.

Filter 802 may be configured to transmit the emitted fluorescent light from the eye's fundus towards an image detector unit 18, while blocking the excitation illumination spectrum thus being operative while in the FA mode. In this case, the FA barrier filter 802 is displaceable between its operative position (in the optical path) and inoperative position (out of the optical path) and can be replaced by the ICG barrier filter in a consecutive manner.

As indicated above, filter 802 is preferably configured as a dual spectrum barrier filter, namely defines two spectral bandwidths corresponding to both the FA and the ICG procedures. This enables yet another operational mode of system 800, namely taking a combined FA/ICG photo by applying both the visible and the NIR flashes substantially simultaneously (i.e., simultaneously or in a very fast sequence) and directing the resulting image onto CMOS or CCD camera 18 which is sensitive to the spectral range of 400-850 nm. This provides for a very effective diagnostic tool to ophthalmologists, enabling the observation of different layers of the retina and choroid in a single procedure.

Figure 14A:
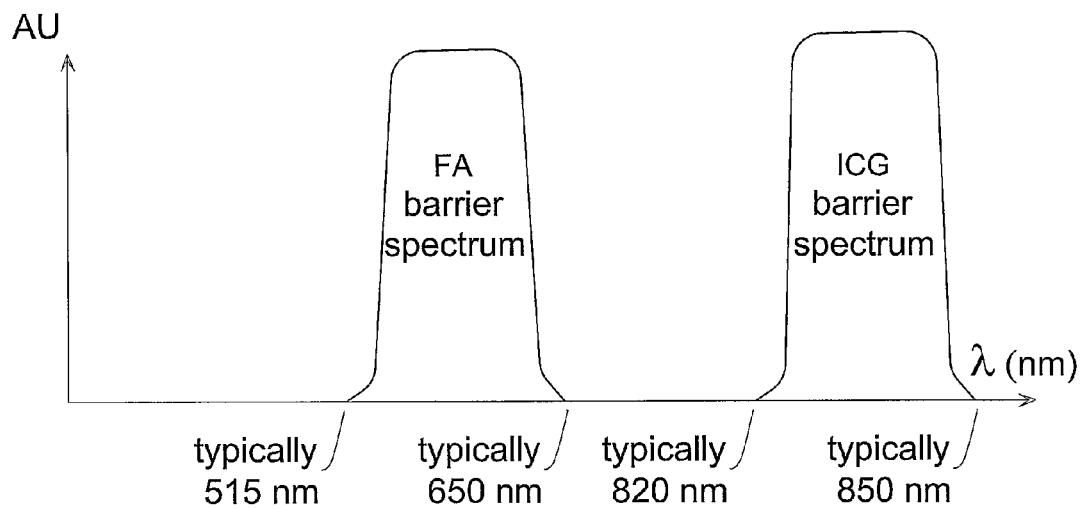
FIGS. 14A and 14B illustrate, respectively, the characteristics of a dual spectral barrier filter for both the FA and ICG emissions, and the spectral characteristics of this filter with respect to the typical fluorescein absorption and emission spectra.
Figure 14B:
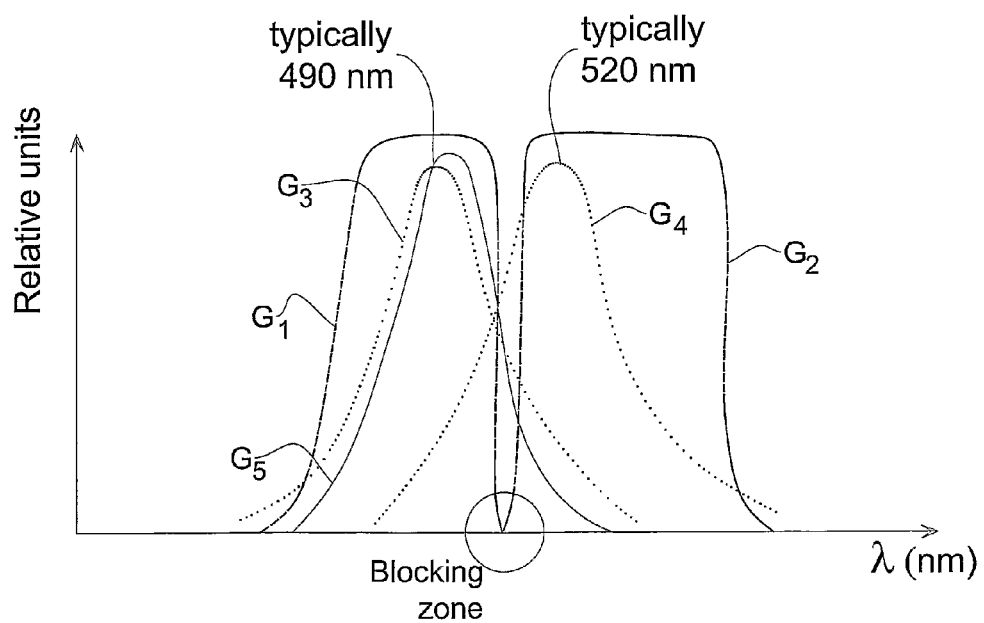

FIG. 14A illustrates the characteristics of such a dual spectral barrier filter. FIG. 14B shows the spectral characteristics of the filter with respect to the typical fluorescein absorption and emission spectra: graphs $G_1$, $G_2$, $G_3$, $G_4$ and $G_5$ correspond to, respectively, the excitation filter, barrier filter, fluorescein absorption, fluorescein emission, and LED emission. As shown, a relation between the LED and fluorescein absorption spectra is characterized by the maximal congruency; a relation between the excitation filter, fluorescein absorption and LED spectra maximizes the energy (highest cut-off); a relation between barrier filter and fluorescent emission maximizes the energy (lowest cut-on); and the excitation filter and barrier filter spectra define a blocking zone (transmission less than 0.01%). The above relations are optimized by using an optimization algorithm from which the LEDs and filters are chosen and designed accordingly.

The invention also provides for the system operation with a fast fluorescence mode. In the current state of the art, a fundus camera is capable of providing either a noisy live image or a flash (pulse) based fluorescence image in a rate of up to 1 or 2 frames per second. The invention utilizes a pulsed light source operable with high-frequency high-intensity light pulses (e.g., at a rate of 10 pulses per second), thus enabling creation of a pseudo live image with multiple-frames per second. In the optimum case, when this number reaches 30 frames per second and this pulse illumination is synchronized with the camera, the same amount of images/second will be created as with a regular direct live image. The inventors have found that this is especially possible with LED's sources that can generate more than 30 pulses (flashes) per second. It is important to note that this cannot be achieved with a Xenon lamp illumination source.

The inventors have found that the high-intensity flash mode operation of a LED can be achieved by applying to the LED a controllable "pumping". This is implemented by applying pulses of high electric current while controlling the electric current maximal value so as not to exceed a predetermined threshold for a specific LED, on the one hand, and keeping the current pulses' shape stabilized and controlled. Hence, the present invention provides for realization of high intensity light for a short flash duration. It is important to note that the technique of the invention utilizes pumping of the LED driving current to up to 12 times of its rating current (according to retailers' catalogues). This can be achieved since the duty-cycle of flashes may be very small (e.g., about 1/50), which permits sufficient time for the LED junction to cool down prior to its next flash action. It should be understood that the flash rate and the flash duration are fully controllable to obtain the desired results (e.g., emitted energy). The current is limited in a fashion that will secure few years of service under the most demanding conditions.

The FA procedure uses fluorescein as a fluorescent material. Based on typical excitation spectrum and typical emission spectrum, the illuminating LED spectrum and the spectra of the excitation and barrier filters are adjusted in a manner that ensures both optimized energy utilization and blocking characteristics to ensure the highest dynamic range and thus the best diagnostic ability from the resulting photos.

The present invention also provides a special mechanism for controlling a light compensation to regulate for ANSI regulations for maximal allowed light. This is implemented as follows: A part of the illumination light is coupled into a separate photodetector, such as a photodiode. The amount of light collected in this detector has a direct linear relation with the amount of light collected by the eye that can be simulated with a detector in the position of the eye, a so-called "eye-simulating detector". By measuring both the energy at the separate photodetector and at the eye-simulating detector, the output at the separate photodetector can be verified when the eye-simulating detector accumulates the maximum amount of light allowed according to the ANSI regulations. During normal operation, light accumulated on the separate photo-detector is integrated on-line till it reaches the maximum amount allowed according to the ANSI regulations reduced by a certain safety margin. Then, this photodetector or a control unit associated therewith sends a trigger to stop the illumination (to switch off the illuminating device) using additional electronics and or software/hardware.

The present invention, in its yet another aspect, provides for automatic control of the exposure of a region of interest. This is associated with the following: Conventional fundus cameras utilize a film and/or still cameras to photograph various retinal objects. Some of the known fundus cameras utilize video cameras to observe real time images either as eye-piece ocular replacement, especially when a NIR light source (not observable by a human eye) is used, or as an additional image source.

Figure 15:
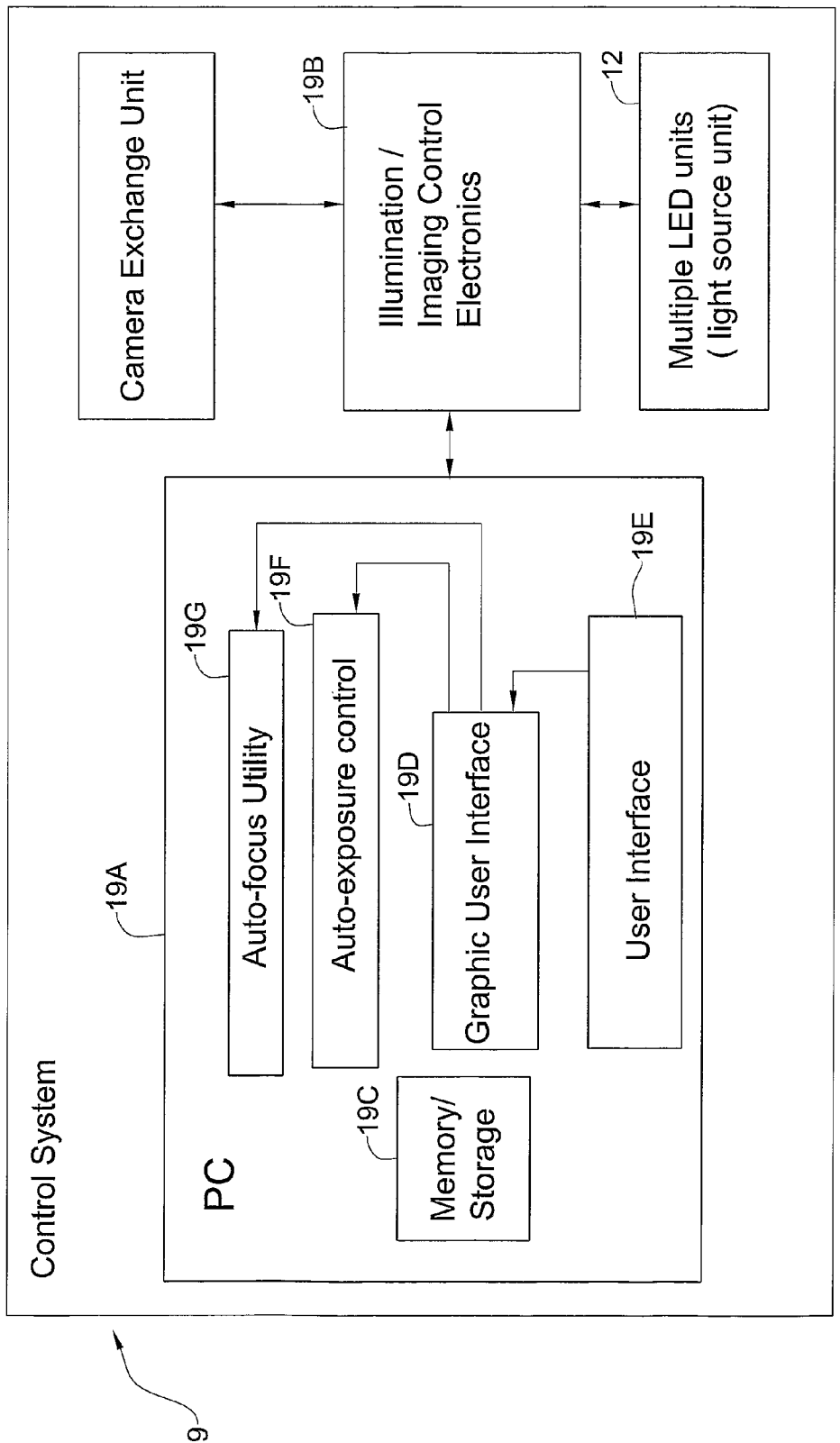
FIG. 15 illustrates a block diagram of a control system for use with the system of FIG. 1A.

FIG. 15 illustrates a block diagram of a control system 19 (referred to in FIG. 1A). Control system is an electronic assembly formed by a computer unit 19A (e.g., a personal computer) and an illumination/imaging control electronics 19B (specifically designed printed circuit board). Also provided in control-system 19 are a camera exchange unit 19C (configured and operable to shift between different cameras) and a multiple LED units' arrangement 12 (i.e., light source unit formed by LEDs and their associated light guides). PC unit 19A typically has a memory/storage utility 19C, and according to the invention is preprogrammed with several models including inter alia a graphic unit interface 19D, an application mode selector 19E, auto-exposure control utility 19F and an auto-focus utility 19G.

It should be noted although not specifically shown that the control system may be configured to make a record for each patient regarding his specific imaging-related data (i.e., colorness/brightness, vision diopters of each of the patient eyes and per application mode, patient eye properties such as eye class, regions of interest in the eye, etc.) and the corresponding patient identification data. Hence, the present invention provides for recording the patient imaging-relayed data at his first examination, and for each further examination enables automatic selection of the exposure settings and focusing lens set per patient eye and clinical mode intended to be used in response to the patient ID data entry.

The present invention utilizes auto-exposure control utility 19F providing a mechanism configured and operable to set appropriate light exposure parameters (such as exposure time, illumination and camera gain) in either one of the application modes, and provides for analyzing the acquired images such as to optimize an image-related data taken by flash (pulsed) light imaging and/or continuous imaging. This can be implemented using default exposures, or by automatic exposure according to the invention.

With regard to the default exposures, the following should be noted: As a fundus camera uses various fluorescent agents, times after injection and magnifications, the optimum illumination parameter strongly varies from application to application. Defining any desired amount of illumination common for all the applications is practically impossible, but only a common wide range of illumination amounts can be defined. However, when using a specific fluorescent agent at a specific time after the injection and with a certain magnification, the range of optimal illumination can be significantly narrowed. Data indicative of desired (optimum) amount of illumination can be determined by capturing images acquired with all the possible variations of input parameters that include magnification, and/or fluorescent agent and/or time after the injection and possibly other data. This desired data combined with the input parameters can be used as reference data, e.g., in the form of LUT (Look-Up-Table). In an automatic illumination mode, software can be designed to use the input parameters to select from the reference data the corresponding desired illumination amount and operate the exposure accordingly. After a time period (exposure time) needed to accumulate the desired amount of light, a CCD or CMOS detector receives a trigger to stop the light collection and/or illumination.

As for the automatic exposure, it can be of a first type consisting of the following: Part of the desired excited (fluorescent) light is coupled into a separate photodetector such as a photodiode. The amount of light collected in this separate detector will have a direct linear relation with the amount of light collected on the CCD or image-capturing device. By analyzing the captured images, a range of light detected at the separate photodetector can be selected as corresponding to well-illuminated images and over-illuminated images. Based on these analyses, the optimum desired light accumulated at the separate photodiode can be set to correspond to the well-illuminated images, and non-illuminated, or very little, over and/or under illuminated images. During normal operation, the light accumulated on the separate photodetector is integrated on-line, till it reaches the optimum light level, and then a trigger signal is generated to stop the light capture and/or to stop the illumination, using additional electronics and/or software/hardware. Hence, controlling of the amount of light collected at the separate photodetector is used for managing the image acquisition procedure.

Another type of the invented automatic exposure technique utilizes the so-called "feed forward" control technique. This consists of using images acquired with continuous and/or pulsed (flash) light mode for optimizing the exposure parameters for successive images of the same or different illumination mode. For example, live motion images observed by the continuous light (white, monochromatic at blue, green, red or NIR) are used as a predictor for the amount of light exposure to be used in the flash (pulsed) light imaging.

Figure 16:
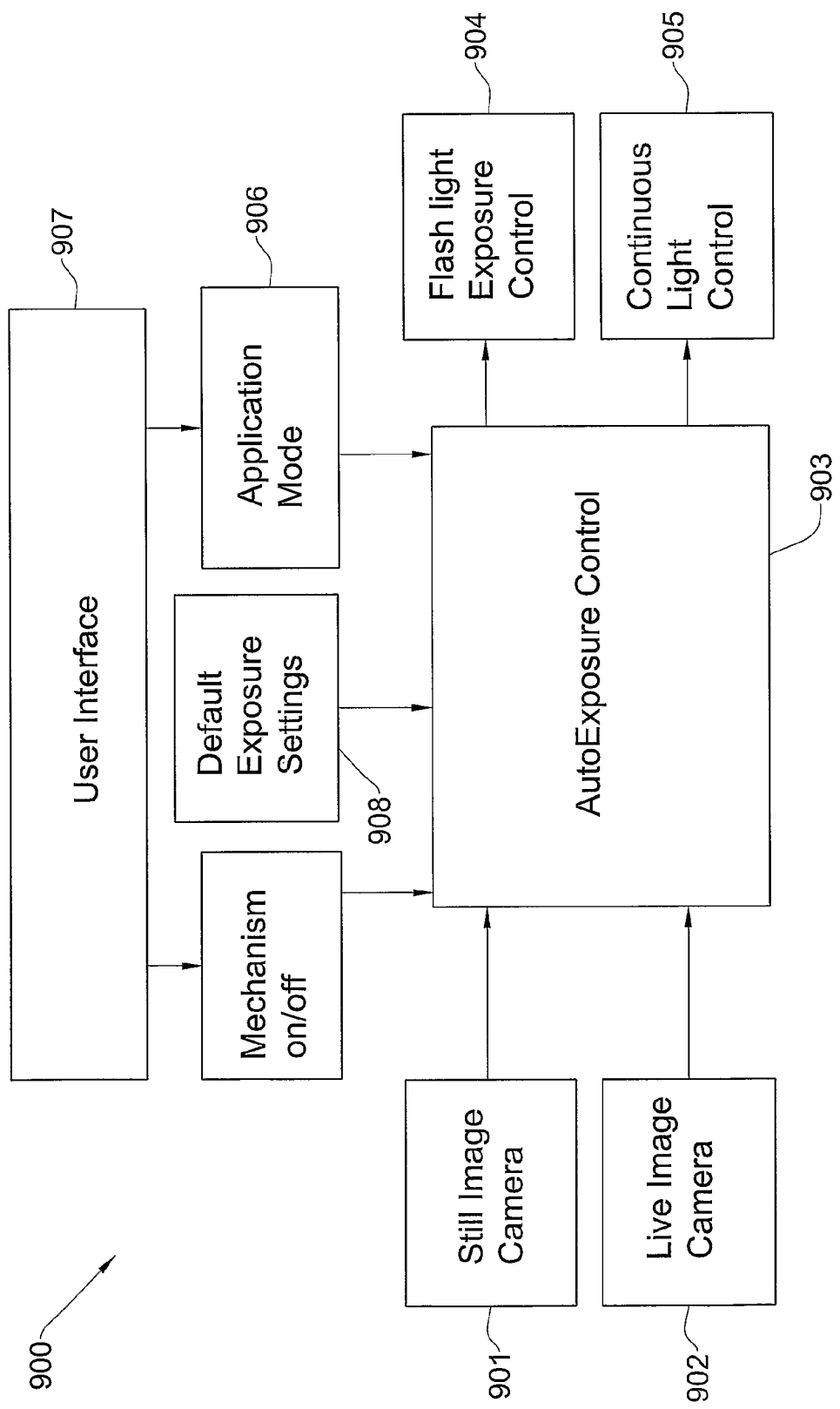
FIGS. 16 and 17 exemplify the principles of the invention for automatic exposure approach.
Figure 17:
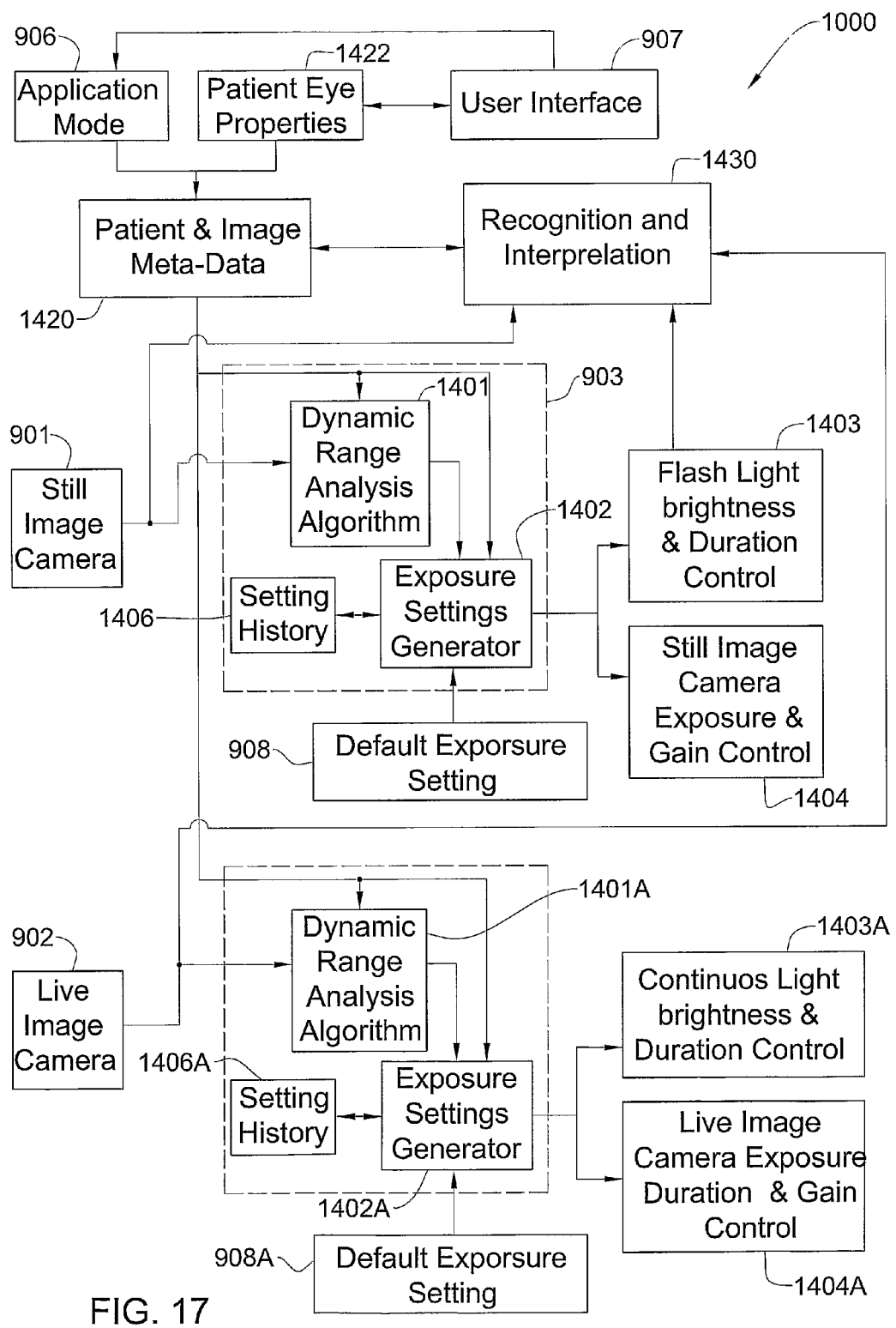

Reference is made to FIG. 16 illustrating a block diagram 900 exemplifying the above-described exposure techniques (auto-exposure control utility 19F in FIG. 15). As shown, data portions indicative of images grabbed by a still image camera 901 and a live image camera 902 are entered into a control unit 903 configured for implementing an auto-exposure control mechanism. An application mode 906, which is determined by user interface 907, sets certain default exposure settings 908, both for a flash light control 904 and for a continuous light control 905. The default values are defined according to a study of the average needs of a patient eye. The auto-exposure control unit 903 is configured as a data processor unit (including software and/or hardware utilities) preprogrammed to analyze the grabbed images, for example by using an image histogram technique with certain parameters that are based on the current application mode 906 and a set of required contrast and density conditions for the image to be obtained. Based on these analyzes, the auto-exposure control unit 903 creates new settings to flash (pulsed) light control 904 and to continuous light control 905. The operation of the auto-exposure unit can be stopped by using an appropriate on/off mechanism 909 operable by a certain default setting and/or manually via user interface 907.

The above-described technique is inter alia suitable for certain applications with dynamic nature such as fluorescein (FA) or Indo-Cyanine-Green Angiography (ICGA), in which the photographic procedure requires a sequence of flash (pulsed light images. Successive images are studied to improve the image total exposure and contrast.

A specific but not limiting example of the above described technique will now be described with reference to FIG. 16 showing a block diagram 1000 of the above concept. Patient & Image Meta-Data 1420 is created from all relevant data about a patient image. This relevant data is obtained during a learning mode and includes inter alia the following: description of an application mode 906 (e.g. color, RF, FA and ICGA, exposure settings, timing information for FA and ICGA application modes); patient eye properties 1422 (e.g., eye class, left/right eye, regions of interest in the eye, etc.). These data portions 906 and 1422 may be obtained from user interface 907, or via a recognition and interpretation module 1430. The latter receives image-related data from cameras 901 (still image camera) and 902 (live image camera). Also the Meta Data 1420 may be based on data coming from exposure settings controls 1403, 1403A, 1404, 1404A, as will be described further below.

With regard to the application mode data, the following should be noted. FA is commonly classified into the following phases according to time elapsed since fluorescein injection (typical durations appear in the literature): pre-arterial phase, transit phase (arterial phase, laminar venous phase, full venous phase), recirculation phase, late phase. ICGA is commonly classified into the following phases according to time elapsed since ICG injection (typical durations appear in the literature): early phase, middle phase, late phase.

The Meta Data 1420 is then utilized in auto-exposure control mechanism formed by units 903 and 903a associated with the two cameras 901 and 902. More specifically, images are obtained with both the still image camera 901 and the live image camera 902; and similar auto-exposure processes are carried out for each camera independently, while both such auto-exposure processes taking advantage of the same Meta Data 1420. The latter presents means for sharing information between the two processing channels (pulse-like and continuous illumination based images).

Captured images (at least some of them), acquired by either one or both cameras 901 and 902, are analyzed by dynamic range analysis algorithms 1401 and 1401A which will be described further below. The output of these algorithms serve as the input for exposure settings generators 1402 and 1402A (also described more specifically further below), which translate the computer-level image processing parameters into system physical parameters that need to be set. These are transmitted to appropriate control units 1403, 1403A, 1404 and 1404A. In this connection, the following should be noted: The exposure settings generator (1402, 1402a) utilizes data indicative of the exposure settings that were used for the image acquisition (the image processed by dynamic range analysis algorithms 1401, 1401a). This could be achieved by "remembering" the last generated settings (as shown in the figure), or although not specifically shown, by getting this as input. The latter case can be implemented by getting this info separately and in addition to the image and the meta-data, or by getting this info as part of the meta-data.

If or when a new image arrives, while the previous one is still being processed, the processing is not halted, but rather a request is placed in a queue or ignored. This allows auto-exposure to be carried out for fast image streams.

Recognition and interpretation module 1430 is configured and operable as follows: Images, taken by both the still and live image cameras 901 and 902, are processed by this module. The algorithms of this module 1430 analyze the image contents and characteristics of objects in the image by utilizing any known suitable computer vision techniques. Output of these algorithms may be indicative inter alia of left/right eye; locations of eye parts such as ONH, macula and blood vessels; eye class (according to a proper eye classification).

Dynamic range analysis algorithms 1401 and 1401A consist of the following: Such algorithm analyzes the dynamic range exploited by the image, and compares it to a theoretical dynamic range (reference data or certain model). Then, recommendations are produced for improving the image dynamic range. The recommendations are given by specifying a source intensity level (src) existing in the image, and a destination intensity level (dst) it should be translated into. For example, if the image is overexposed, a value of dst being less than src is expected. If the image is underexposed, dst being higher than src is expected. Additional parameters may be reported by the algorithm, to indicate the recommended dynamic range improvements.

If the input image has three color channels (RGB), each channel is typically processed independently, and the results are fused together. Also, the algorithm may take advantage of accompanying meta-data, such as the location of eye parts, and regions of interest in the image.

The dynamic range analysis algorithm might create a histogram of the image intensity level, and decide upon a criterion, according to which a certain percentage of the image pixels should have an intensity level greater than a certain percentage of the dynamic range. This criterion may be combined with other requirements such as paying attention only to a certain region of interest.

If the image is saturated, the dynamic range analysis algorithm might choose src and dst according to the percentage of image pixels which are saturated, utilizing a given LUT. For example, keeping src as the 100% dynamic range intensity level, dst will be set to an intensity level proportional to the percentage of non-saturated image pixels.

The dynamic range analysis algorithm may perform linear and/or non-linear pre-processing of the image.

The dynamic range analysis algorithm may also analyze the noise level in the image and pass the results on to the Exposure Settings Generator (1402 and 1402a) for consideration. If the noise source has been identified (such as electronic noise or reflectance), the appropriate exposure settings parameters are altered to reduce the noise level in the image. A search method may be used to find the optimal exposure settings (i.e., those providing best combination of good dynamic range and low noise), even if these settings differ from those imposed by the priority LUT (reference data).

Exposure settings generators 1402 and 1402A are configured and operable as follows: After recommendations have been produced for improving the image dynamic range, they are translated into recommendations for improving the exposure settings of the fundus camera system. These typically include: illumination brightness, exposure duration assuming full illumination, and electronic gain. It should be understood that the phrase "exposure duration assuming full illumination" refers to the exposure duration of flash imaging when a camera shutter is open and flash is illuminating, simultaneously. The exposure settings generator is aimed at: controlling the modification of the different exposure parameters, by following given prioritizing guidelines, thus enabling to achieve the best image quality, best patient comfort, and/or other goals; and selecting the optimal exposure settings in order to minimize, or even eliminate, the need for recurrent exposure corrections.

Figure 18A:
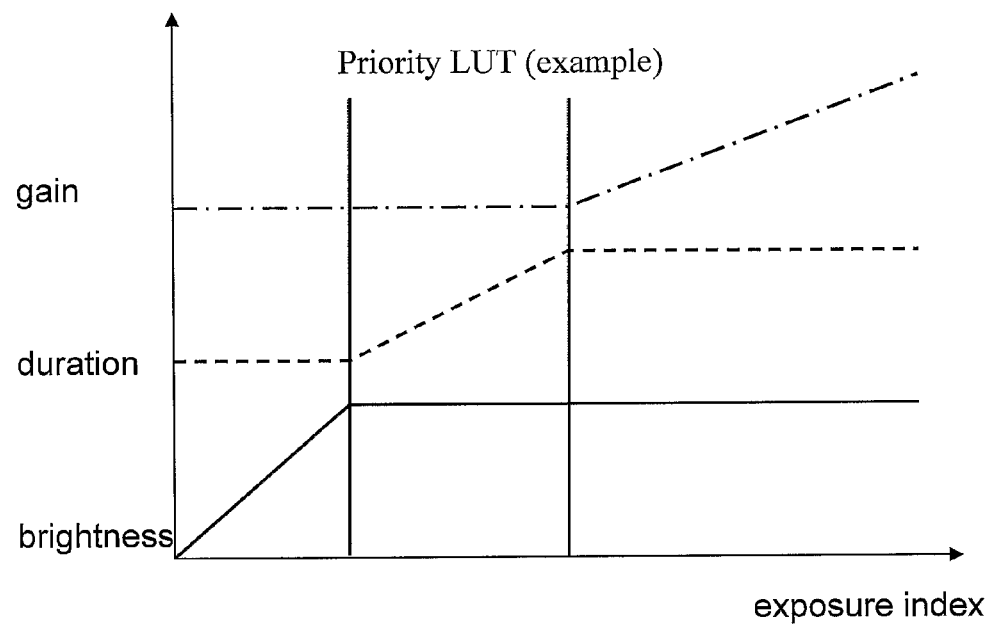

The control of the modification of different exposure parameters is achieved by using LUTs and/or logics describing the priorities of the exposure parameters. Priorities are described for each pair of camera and fundus separately. FIG. 18A shows an example to provide this information. Here, the horizontal axis needs not be of a consistent scale, as an iterative calculation is carried out each time.

Figure 18B:
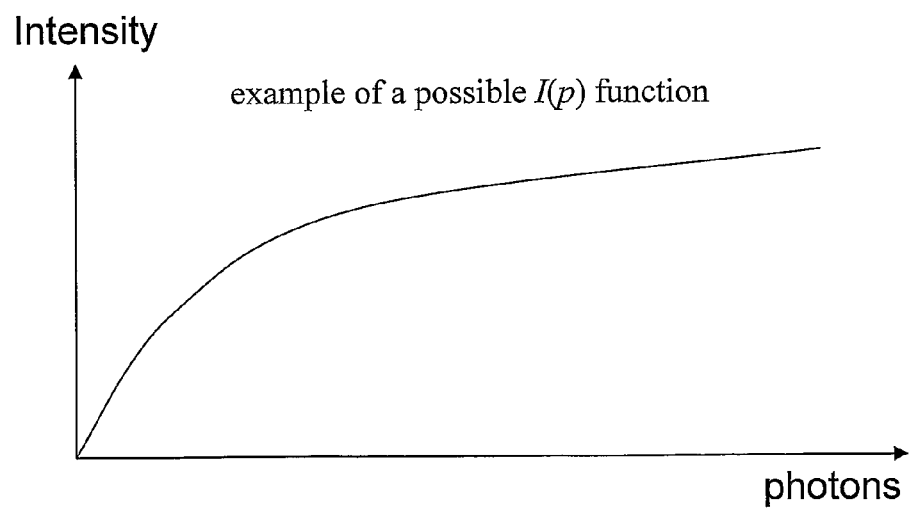
FIG. 18B shows an example of a non-linear dependency of pixel intensity on the number of photons hitting the detector.

The selection of the optimal exposure settings is achieved by knowing the effect of the exposure settings on the captured image. All relevant characteristic behaviors of the camera and/or fundus are given as LUTs or integrated into the logic of the exposure settings generator. FIG. 18B shows an example of a non-linear dependency of pixel intensity on the number of photons hitting the detector.

In some cases, default exposure settings 908, 908A are used according to given meta-data. The default exposure settings might also limit the range of the automatically calculated exposure settings or be weighted together with them. The exposure settings generator may use history-data saved in dedicated memory locations 1406 and 1406A, in order to achieve better stabilization and/or minimization of the number of recurrent cycles needed for achieving proper exposure.

Thus, the present invention provides for a novel effective configuration of an imager, particularly useful as an integrated retina imager, and method of its operation and control. Those skilled in the art will readily appreciate that various modifications and changes can be applied to the embodiments of the invention as hereinbefore described without departing from its scope defined in and by the appended claims.

The invention claimed is:
1. A system for use in imaging the patient's retina, the system comprising:
(a) a light source unit comprising at least one ring-like shaped member carrying multiple light emitting diodes (LEDs) arranged in a circular array and producing together at least one ring-like shaped light beam, the arrangement of LEDs comprising multiple LEDs of dif- ferent wavelength ranges, of which at least one LED is adapted for emitting light in a near infrared spectral range; and (b) a light directing optics for directing the at least one ring-like shaped light beam towards a region on the retina being illuminated and for collecting and directing light returned from the illuminated region to an image detector unit.

2. The system of claim 1, wherein said LED arrangement comprises at least one LED emitting light in a visible spectral range.

3. The system of claim 1, wherein the light source unit comprises at least one laser diode.

4. The system of claim 1, wherein the LED arrangement generates light of at least Red, Green, Blue and White colors.

5. The system of claim 1, wherein the light directing optics comprises at least one of the following: (1) a condenser lens arrangement in the optical path of light emitted by the LED arrangement; (2) a field lens arrangement in the optical path of the illuminating light; (3) a relay lens arrangement in the optical path of the illuminating light; and (4) a beam combiner in the form of a mirror with hole for reflecting the illuminating light by its periphery reflective region, and transmitting the returned light through the central hole.

6. The system of claim 5, wherein said hole has a dimension defined by the eye pupil size and a magnification of an objective lens arrangement.

7. The system of claim 1, comprising a light guide arrangement having at least one of the following configurations: (i) comprising one or more light guide unit each configured as a cone-like reflector; and (ii) comprising one or more light guide units each configured to provide the illuminating light beam cone of about 20 degrees or less at the output thereof.

8. The system of claim 7, wherein the light guide unit has a parabolic-like curvature of its inner reflective surface.

9. The system of claim 7, wherein the light source unit comprises an adaptor unit carrying the LED arrangement and being configured and operable for selectively shifting one or more of the LEDs into an operation mode.

10. The system of claim 9, wherein said adaptor unit comprises: at least one first light unit formed by the first light guide unit carrying at its one end the first LED operating in a near infrared range and its other end carrying a first condenser lens arrangement; and at least two second light units each formed by the second light guide unit carrying at its one end the second LED operating in a visible spectral range and carrying a second condenser lens arrangement; the second light unit being arranged along an axis intersecting with the first light unit thereby enabling to combine the first and second light paths; said at least two second light units being mounted on a member rotating with respect to said first light unit.

11. The system of claim 10, wherein said adaptor unit comprises a wavelength-selective arrangement accommodated at the intersection between the first and second optical paths.

12. The system of claim 11, wherein said wavelength-selective arrangement is configured to reflect visible light and transmit NIR light.

13. The system of claim 10, wherein said adaptor unit comprises the multiple second light units containing the LEDs emitting different wavelengths of the visible range.

14. The system of claim 1, wherein an aperture formed by said ring-like shaped light beam defines an imaging channel for said returned light propagation.

15. The system of claim 1, comprising a mask assembly located in the optical path of the illuminating light, said mask assembly being configured to define at least two masks of different patterns, each pattern defining a ring-like shaped light transmitting path.

16. The system of claim 1, wherein the light source unit comprises diffractive or refractive optics accommodated in the optical path of light emitted by at least one LED and operating to provide high efficient coupling of Lambertian light into a ring, thereby producing said at least one ring-like shaped light beam.

17. The system of claim 1, wherein the LED arrangement of the light source unit comprises at least two LED assemblies, each LED assembly comprising multiple LEDs coupled to the common light guide configured for coupling light from said multiple LEDs into a single ring-like light beam; the light directing optics comprising a wavelength-selective arrangement including at least one wavelength-selective filter for combining light from said at least two light assemblies.

18. The system of claim 1, wherein the locally adjacent LEDs in the circular array differ from each other in at least one of emitting spectra and power.

19. The system of claim 1, wherein the LEDs array contains different groups of LEDs, wherein the LEDs of each group are substantially identical in at least one of spectrum and power, and different from that of the other group.

20. The system of claim 1, wherein the LED arrangement comprises at least two said LED assemblies; the light directing optics comprising a wavelength-selective arrangement including at least one wavelength-selective filter for combining light from said at least two light assemblies.

21. The system of claim 1, wherein at least some of the LEDs are associated with a condenser lens arrangement configured to narrow an emitting angle of light emitted by the LED.

22. The system of claim 1, wherein at least some of the LEDs are associated with a light diffusing element, thereby providing substantially uniform illumination of said illuminating light beam.

23. The system of claim 1, comprising at least one micro lens array configured to condense or diffuse light emitted by at least some of the LEDs in the circular array.

24. The system of claim 1, wherein the LED arrangement comprises at least two LED assemblies emitting light of, respectively, exciting and visible wavelength ranges; the system comprising at least one spectral filter accommodated in the optical path of the returned light.

25. The system of claim 24, wherein the spectral filter is configured for transmitting excited light, created in the eye region in response to said exciting light, and blocking the exciting light.

26. The system of claim 25, wherein the spectral filter is displaceable between its operating position being in the optical path of returned light and its inoperative position being outside of said optical path.

27. The system of claim 24, wherein the spectral filter is configured as a dual spectrum barrier filter defining two spectral bandwidths corresponding to those used for, respectively, fluorescein (FA) and Indo-Cyanine Green (ICG) angiography, thereby enabling to obtain FA and ICG images by applying visible illumination and NIR flashes at least quasi-simultaneously.

28. The system of claim 27, wherein the image detector unit comprises a CMOS or CCD image detector sensitive to a 400-850 nm spectral range.

29. The system of claim 1, wherein the light source unit comprises one or more LEDs operating in a pulsed mode.

30. The system of claim 29, wherein the pulsed mode light source unit operates with up to 30 or more frames per second.

31. The system of claim 29, wherein the light source unit comprises one or more LEDs operating in a continuous illumination mode.

32. The system of claim 31, comprising a control system connectable to the light source unit and to the image detector unit, and configured for analyzing images acquired with the pulse and continuous modes to set appropriate light exposure parameters in either one of the application modes or both of them.

33. The system of claim 32, wherein the control system is configured and operable to analyze data indicative of the images acquired with the continuous light mode to utilize this data for optimizing at least one of the light exposure parameters to be used in the pulsed mode imaging.

34. The system of claim 32, wherein said control system is configured for analyzing data indicative of the successively acquired pulse mode images to thereby improve pulse mode image total exposure and contrast.

35. The system of claim 32, wherein said control system is configured for analyzing data indicative of the images acquired with the continuous light mode to thereby improve continuous light mode images total exposure and contrast.

36. A system for use in imaging the patient's retina, the system comprising a light source unit configured for producing at least one ring-like shaped light beam from light emitted by the arrangement of LEDs, the light source unit comprising at least one integrating sphere that carries the multiple LEDs of at least one LED assembly of said LED arrangement and is formed with a ring-like window for the light output, the integrating sphere being configured to recycle light emitted by the LEDs by internal reflection in the integrating sphere.

37. The system of claim 36, wherein an inner surface of said window has a reflective coating.

38. The system of claim 36, wherein the light source unit comprises an external mask positioned so as to cover an inner diameter of the window.

39. The system of claim 36, wherein the light source unit comprises a light-guide accommodated at said window and configured for narrowing light exit angles of the ring-shaped window to match those acceptable by an objective lens arrangement.

40. The system of claim 36, wherein said integrating sphere contains light from multiple different wavelength channels.

41. The system of claim 36, wherein the LED arrangement comprises at least two said LED assemblies; the light directing optics comprising a wavelength-selective arrangement including at least one wavelength-selective filter for combining light from said at least two light assemblies.

42. A method for use in imaging the patient's retina, the method comprising: producing at least one ring-shaped light beam comprising light of multiple different wavelengths emitted by a light emitting diode (LED) arrangement, said LED arrangement comprising at least one ring-like shape member carrying the multiple LEDs of at least one LED assembly arranged in a circular array; directing said ring-like shaped light beam towards a region of the retina and collecting light returned from the illuminated region through the same objective lens arrangement; imaging the collected returned light onto an image detector unit, while controllably operating the image detector unit to selectively detect the retina image by a different image detector.

43. The method of claim 42, controllably operating the LED arrangement to selectively displace one or more LED assemblies of said LED arrangement into an operational mode.

44. The method of claim 42, comprising operating at least some of LEDs in a pulsed illumination mode.

45. The method of claim 44, wherein said operating of at least some LEDs in the pulsed illumination mode comprising pumping each of these LEDs by one or more pulses of electric current while controlling the electric current value, so as to provide maximal emitted energy of the LED, thereby providing fast and effective pulsed mode operation.

46. The method of claim 44, comprising controlling the LED arrangement operation by providing predetermined exposure settings for the pulsed light illumination and the continuous light illumination, providing data indicative of images acquired with the pulsed and continuous illumination modes, analyzing said data based on said predetermined exposure settings, and determining a new exposure settings to the pulsed light control and the continuous light control, thereby enabling to utilize the continuous light measured data to predict amount of light exposure to be used in the pulsed light illumination.

47. The method of claim 42, comprising carrying out at least one of the following: operating at least some of LEDs in a continuous illumination mode; selectively operating the same LED in a pulse or continuous illumination mode.

48. The method of claim 42, comprising concurrent or quasi-concurrently operating the different wavelengths LEDs to produce FA and ICG exciting illumination.

49. The method of claim 42, wherein said directing of the LEDs output light towards the region on the retina comprising combining a first optical path of the NIR LED light with a second optical path of the visible LED light.

50. The method of claim 49, comprising selectively bringing the different visible LED to said second optical path.

51. The method of claim 42, comprising operating the LED arrangement in an FA mode by generating light of a Cyan color, thereby providing optimal excitation of fluorescein.

52. The method of claim 51, wherein said Cyan color is of a 485 nm-500 nm wavelength range.

53. A light source unit for use in an imaging system, the light source unit comprising at least one ring-like shaped member carrying at least one assembly of multiple light emitting diodes (LEDs) comprising LEDs of different wavelength ranges, of which at least one LED is adapted for emitting light in a near infrared spectral range, the multiple LEDs being arranged in a spaced-apart relationship in a circular array for producing together a ring-like shaped light beam, a central hole of the ring-like member for use as an imaging channel for passing therethrough light returned form an illuminated region.

* * * * *